(12) United States Patent
Ryu et al.

(10) Patent No.: US 11,527,026 B2
(45) Date of Patent: Dec. 13, 2022

(54) BODY MEASUREMENT DEVICE AND METHOD FOR CONTROLLING THE SAME

(71) Applicant: LG ELECTRONICS INC., Seoul (KR)

(72) Inventors: Eunkyung Ryu, Seoul (KR); Wonju Lee, Seoul (KR); Fataliyev Zaur, Seoul (KR); Hyunsu Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 17/006,460

(22) Filed: Aug. 28, 2020

(65) Prior Publication Data

US 2021/0256747 A1    Aug. 19, 2021

Related U.S. Application Data

(60) Provisional application No. 62/894,846, filed on Sep. 1, 2019.

(30) Foreign Application Priority Data

Jan. 6, 2020   (WO) ................ PCT/KR2020/000213

(51) Int. Cl.
| | | |
|---|---|---|
| *G06T 11/60* | (2006.01) | |
| *G06T 7/55* | (2017.01) | |
| *G06T 7/62* | (2017.01) | |
| *G06T 7/73* | (2017.01) | |
| *H04N 5/232* | (2006.01) | |

(52) U.S. Cl.
CPC ............. *G06T 11/60* (2013.01); *G06T 7/55* (2017.01); *G06T 7/62* (2017.01); *G06T 7/75* (2017.01); *H04N 5/23229* (2013.01); *G06T 2207/10024* (2013.01); *G06T 2207/10028* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 2016/0110595 A1* | 4/2016 | Wang | G06K 9/6201 |
| | | | 705/27.2 |
| 2018/0039745 A1* | 2/2018 | Chevalier | G16H 10/60 |

FOREIGN PATENT DOCUMENTS

| | | |
|---|---|---|
| KR | 101436322 | 10/2014 |
| KR | 1020160041965 | 4/2016 |
| KR | 1020160110070 | 9/2016 |
| WO | 2013/189058 | 12/2013 |
| WO | 2017/031889 | 3/2017 |

OTHER PUBLICATIONS

PCT International Application No. PCT/KR2020/000213, International Search Report dated May 29, 2010, 4 pages.

* cited by examiner

*Primary Examiner* — Heather R Jones
(74) *Attorney, Agent, or Firm* — Lee, Hong, Degerman, Kang & Waimey PC

(57) ABSTRACT

To measure a body size with increased convenience, a body measurement device including a camera configured to capture an image that includes an RGB image and a depth image, a display, and a controller configured to acquire a source image that includes a skeleton image and a body line image of a user based on the captured image, acquire a body size including a body height based on the source image, and control the display to display the body size is provided.

10 Claims, 34 Drawing Sheets

FIG. 6A
FIG. 6B
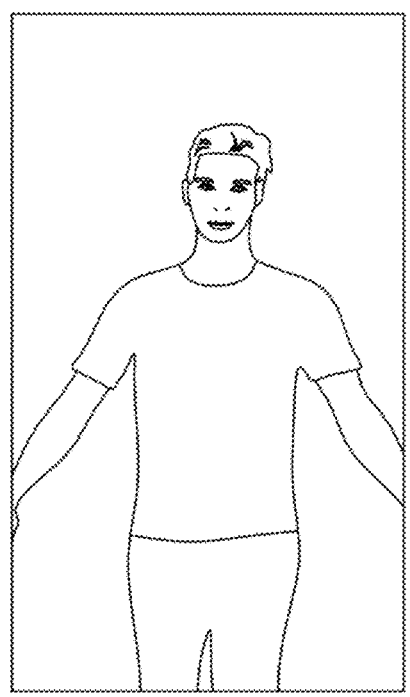
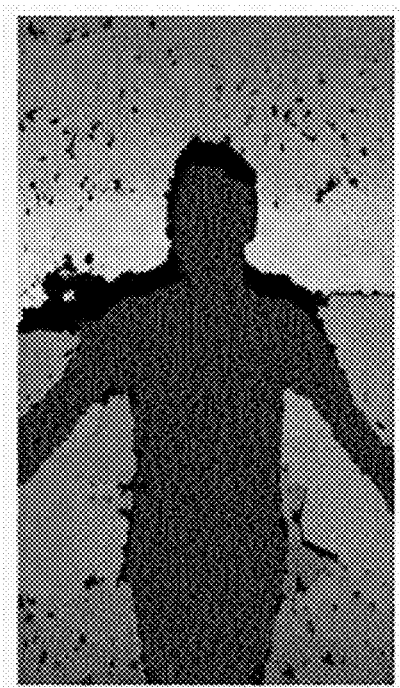
RGB
Depth

FIG. 17A
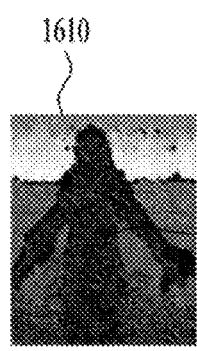
FIG. 17B
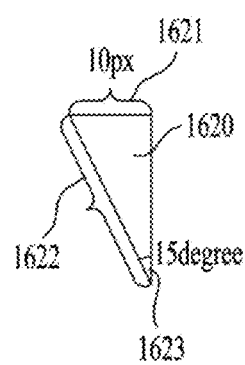
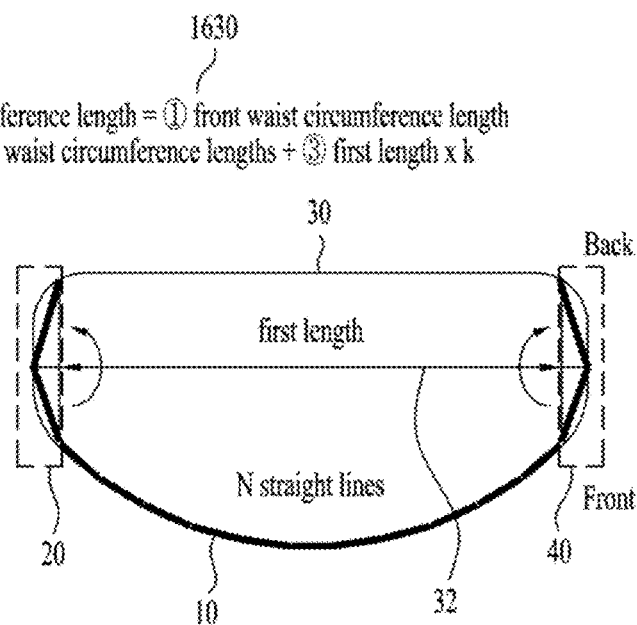

FIG. 18

| Height | user name | | | | | Error Calculation(RMSE) | | | | RMSE avg |
|---|---|---|---|---|---|---|---|---|---|---|
| | CHC | UEN | ZF | WJU | PSO | | | | | |
| Actual | 1.78 | 1.6 | 1.72 | 1.73 | 1.79 | | | | | |
| M-1 | 1.78202 | 1.60991 | 1.72263 | 1.74325 | 1.79694 | 0.002 | 0.010 | 0.006 | 0.013 | 0.007 | |
| M-2 | 1.77908 | 1.61356 | 1.72681 | 1.74313 | 1.79634 | -0.001 | 0.014 | 0.007 | 0.013 | 0.006 | |
| M-3 | 1.76101 | 1.61339 | 1.72393 | 1.73632 | 1.79752 | -0.019 | 0.013 | 0.004 | 0.006 | 0.008 | |
| M-4 | 1.79096 | 1.6109 | 1.72185 | 1.73205 | 1.78233 | 0.011 | 0.011 | 0.002 | 0.002 | -0.008 | |
| M-5 | 1.79273 | 1.61307 | 1.72935 | 1.73541 | 1.78466 | 0.013 | 0.013 | 0.009 | 0.005 | -0.005 | |
| M-6 | 1.80618 | 1.60023 | 1.72428 | 1.74063 | 1.78558 | 0.026 | 0.000 | 0.004 | 0.011 | -0.004 | |
| M-7 | 1.79411 | 1.60968 | 1.73279 | 1.74691 | 1.78769 | 0.014 | 0.010 | 0.013 | 0.017 | -0.002 | |
| M-8 | 1.7981 | 1.61075 | 1.72398 | 1.73873 | 1.78805 | 0.018 | 0.011 | 0.004 | 0.009 | -0.002 | |
| M-9 | 1.79534 | 1.61064 | 1.7269 | 1.73734 | 1.78826 | 0.015 | 0.011 | 0.007 | 0.007 | -0.002 | |
| M-10 | 1.79728 | 1.60886 | 1.72002 | 1.74383 | 1.78551 | 0.017 | 0.009 | 0.000 | 0.014 | -0.004 | |
| | | | | | | 0.015 | 0.011 | 0.007 | 0.011 | 0.005 | 0.010 |

FIG. 19

| Bust | CHC | UEN | ZF | WJU | PSO | Error Calculation(RMSE) | | | | RMSE (AVG) |
|---|---|---|---|---|---|---|---|---|---|---|
| Actual | 0.98 | 0.89 | 1 | 0.94 | 0.96 | | | | | |
| M-1 | 1.04009 | 0.845361 | 1.01695 | 1.03972 | 1.04331 | 0.060 | -0.045 | 0.017 | 0.100 | 0.083 |
| M-2 | 1.02241 | 0.869981 | 1.03189 | 1.04818 | 1.04769 | 0.042 | -0.020 | 0.032 | 0.108 | 0.088 |
| M-3 | 1.00679 | 0.86586 | 1.00939 | 1.07036 | 1.05141 | 0.027 | -0.024 | 0.009 | 0.130 | 0.091 |
| M-4 | 1.01789 | 0.831692 | 1.03495 | 1.04446 | 1.05655 | 0.038 | -0.058 | 0.035 | 0.104 | 0.097 |
| M-5 | 1.01635 | 0.865205 | 0.993069 | 1.04071 | 1.0428 | 0.036 | -0.025 | -0.007 | 0.101 | 0.083 |
| M-6 | 1.00383 | 0.868732 | 1.02785 | 1.02811 | 1.04623 | 0.024 | -0.021 | 0.028 | 0.088 | 0.086 |
| M-7 | 0.994472 | 0.859791 | 1.04227 | 1.02043 | 1.0785 | 0.014 | -0.030 | 0.042 | 0.080 | 0.119 |
| M-8 | 0.986781 | 0.862848 | 0.994109 | 1.02206 | 1.07133 | 0.007 | -0.027 | -0.006 | 0.082 | 0.111 |
| M-9 | 1.00733 | 0.873891 | 1.0031 | 1.01734 | 1.06989 | 0.027 | -0.016 | 0.003 | 0.077 | 0.111 |
| M-10 | 0.980569 | 0.885662 | 1.06355 | 1.04747 | 1.07531 | 0.001 | -0.004 | 0.064 | 0.107 | 0.115 |
| | | | | | | 0.032 | 0.031 | 0.031 | 0.099 | 0.099 |
| | | | | | | | | | | 0.058 |

FIG. 20

| Undertrust | CHC | UEN | ZF | WJU | PSO | Error Calculation(RMSE) | | | | RMSE (AVG) |
|---|---|---|---|---|---|---|---|---|---|---|
| Actual | 0.88 | 0.76 | 0.92 | 0.81 | 0.87 | | | | | |
| M-1 | 0.959572 | 0.740597 | 0.891556 | 0.845364 | 0.815112 | 0.080 | -0.019 | -0.028 | 0.035 | -0.055 |
| M-2 | 0.960445 | 0.778881 | 0.934841 | 0.837927 | 0.81219 | 0.080 | 0.017 | 0.015 | 0.028 | -0.058 |
| M-3 | 0.885358 | 0.747397 | 0.883519 | 0.83848 | 0.816697 | 0.005 | -0.013 | -0.036 | 0.028 | -0.053 |
| M-4 | 0.869253 | 0.746978 | 0.89718 | 0.848899 | 0.843954 | -0.011 | -0.013 | -0.023 | 0.039 | -0.026 |
| M-5 | 0.903299 | 0.728595 | 0.916648 | 0.835069 | 0.84289 | 0.023 | -0.031 | -0.003 | 0.025 | -0.027 |
| M-6 | 0.854477 | 0.796582 | 0.905937 | 0.842107 | 0.85982 | -0.026 | 0.037 | -0.014 | 0.032 | -0.010 |
| M-7 | 0.889031 | 0.729862 | 0.90858 | 0.888561 | 0.834572 | 0.009 | -0.030 | -0.011 | 0.079 | -0.035 |
| M-8 | 0.842965 | 0.722918 | 0.902044 | 0.887559 | 0.833374 | -0.037 | -0.036 | -0.018 | 0.078 | -0.037 |
| M-9 | 0.895525 | 0.768041 | 0.930673 | 0.881202 | 0.849877 | 0.016 | 0.008 | 0.011 | 0.071 | -0.020 |
| M-10 | 0.880604 | 0.892004 | 0.920384 | 0.910196 | 0.850542 | 0.001 | 0.132 | 0.000 | 0.100 | -0.019 |
| | | | | | | 0.040 | 0.048 | 0.019 | 0.058 | 0.038 | 0.040 |

FIG. 21

| Want Actual | user name ||||| Error Calculation (RMSE) |||| RMSE (AVG) |
|---|---|---|---|---|---|---|---|---|---|---|
| | CHC | UEN | ZF | WU | PSO | | | | | |
| | 0.92 | 0.79 | 0.94 | 0.84 | 0.89 | | | | | |
| M-1 | 0.985915 | 0.774177 | 0.984153 | 0.848072 | 0.900526 | 0.066 | -0.016 | 0.044 | -0.002 | 0.011 |
| M-2 | 0.93938 | 0.805008 | 0.98209 | 0.853858 | 0.905829 | 0.019 | 0.015 | 0.042 | 0.014 | 0.016 |
| M-3 | 0.9291 | 0.760689 | 0.985581 | 0.835804 | 0.903069 | 0.009 | -0.029 | 0.046 | -0.004 | 0.013 |
| M-4 | 0.910563 | 0.807643 | 0.992744 | 0.839989 | 0.886952 | -0.009 | 0.018 | 0.053 | 0.000 | -0.003 |
| M-5 | 0.914214 | 0.785268 | 0.978708 | 0.834117 | 0.882578 | -0.006 | -0.005 | 0.039 | -0.006 | -0.007 |
| M-6 | 0.94594 | 0.787401 | 0.981236 | 0.832429 | 0.892524 | 0.026 | -0.003 | 0.041 | -0.008 | 0.003 |
| M-7 | 0.937745 | 0.798734 | 0.956084 | 0.86407 | 0.894294 | 0.018 | 0.009 | 0.016 | 0.024 | 0.004 |
| M-8 | 0.923961 | 0.796514 | 0.956574 | 0.857371 | 0.890259 | 0.004 | 0.007 | 0.017 | 0.017 | 0.000 |
| M-9 | 0.935742 | 0.814224 | 0.959674 | 0.865305 | 0.888368 | 0.016 | 0.024 | 0.020 | 0.025 | -0.002 |
| M-10 | 0.915117 | 0.801508 | 0.965981 | 0.873676 | 0.893012 | -0.005 | 0.012 | 0.026 | 0.034 | 0.003 |
| | | | | | | 0.025 | 0.016 | 0.037 | 0.017 | 0.008 |
| | | | | | | | | | | 0.020 |

FIG. 22

| Hp | CHC | UEN | ZF | WU | PSQ | Error Calculation(RMSE) | | | | RMSE (AVG) |
|---|---|---|---|---|---|---|---|---|---|---|
| Actual | 0.99 | 0.94 | 1.02 | 0.95 | 1.01 | | | | | |
| M-1 | 1.09757 | 0.944828 | 1.04016 | 0.980336 | 1.03129 | 0.108 | 0.005 | 0.020 | 0.030 | 0.021 |
| M-2 | 1.06528 | 0.945188 | 1.05617 | 1.01488 | 1.03306 | -0.032 | 0.000 | 0.016 | 0.035 | 0.002 |
| M-3 | 1.0606 | 0.956096 | 1.05953 | 0.976487 | 1.03951 | -0.005 | 0.011 | 0.003 | -0.038 | 0.006 |
| M-4 | 1.04748 | 0.95976 | 1.0458 | 1.0016 | 1.02733 | -0.013 | 0.004 | -0.014 | 0.025 | -0.012 |
| M-5 | 1.04226 | 0.9746 | 1.03926 | 0.987885 | 1.03579 | -0.005 | 0.015 | -0.007 | -0.014 | 0.008 |
| M-6 | 1.0607 | 0.968973 | 1.00894 | 0.982493 | 1.03653 | 0.018 | -0.006 | -0.030 | -0.005 | 0.001 |
| M-7 | 1.05899 | 0.951048 | 1.0308 | 0.987858 | 1.04057 | -0.002 | -0.018 | 0.022 | 0.005 | 0.004 |
| M-8 | 1.0321 | 0.961209 | 1.00953 | 0.991284 | 1.04747 | -0.027 | 0.010 | -0.021 | 0.003 | 0.007 |
| M-9 | 1.05634 | 0.9737 | 1.01427 | 1.0077 | 1.04038 | 0.024 | 0.012 | 0.005 | 0.016 | -0.007 |
| M-10 | 1.03009 | 0.966849 | 1.00704 | 1.02772 | 1.03339 | -0.026 | -0.007 | -0.007 | 0.020 | -0.007 |
| | | | | | | 0.039 | 0.010 | 0.017 | 0.023 | 0.009 | 0.019606 | user name

FIG. 23

| error | | | | |
|---|---|---|---|---|
| height | Bust circumference | underbust circumference | waist circumference | hip circumference |
| 0.6% | 6.1% | 4.9% | 2.3% | 2.0% |

| accuracy | | | | |
|---|---|---|---|---|
| height | Bust circumference | underbust circumference | waist circumference | hip circumference |
| 99.4% | 93.9% | 95.1% | 97.7% | 98.0% |

FIG. 24

| (Unit : m) | | Error Calculation(RMSE) | | | Error Calculation(RMSE) | | | error % | | |
|---|---|---|---|---|---|---|---|---|---|---|
| | | Height (length) | Shoulder (length) | Arm (length) | Height (length) | Shoulder (length) | Arm (length) | Height (length) | Shoulder (length) | Arm (length) |
| UEK | Actual | 1.53 | 0.25 | 0.45 | | | | | | |
| | M-1 | 1.52192 | 0.263726 | 0.450191 | 0.00808 | -0.013726 | -0.000191 | | | |
| | M-2 | 1.5304 | 0.26052 | 0.489399 | -0.0004 | -0.01052 | 0.040601 | | | |
| | M-3 | 1.54128 | 0.261508 | 0.485022 | -0.01128 | -0.011508 | 0.044978 | | | |
| | M-4 | 1.53899 | 0.263121 | 0.491977 | -0.00899 | -0.013121 | 0.048023 | | | |
| | M-5 | 1.54272 | 0.271234 | 0.392656 | -0.01272 | -0.021234 | 0.057344 | | | |
| | | | | | 0.00933063 | 0.014522747 | 0.043048905 | 0.006098 | 0.058091 | 0.095664 |
| KBR | Actual | 1.70 | .29 | .52 | | | | | | |
| | M-1 | 1.67122 | 0.29359 | 0.509667 | -0.14122 | -0.04359 | -0.059667 | | | |
| | M-2 | 1.68491 | 0.297406 | 0.52487 | -0.15491 | -0.047406 | -0.07487 | | | |
| | M-3 | 1.66735 | 0.276732 | 0.510197 | -0.13735 | -0.026732 | -0.060197 | | | |
| | M-4 | 1.66946 | 0.281289 | 0.520682 | -0.13946 | -0.031289 | -0.070682 | | | |
| | M-5 | 1.67104 | 0.278205 | 0.494652 | -0.14104 | -0.028205 | -0.044652 | | | |
| | | | | | 0.138533299 | 0.03378227 | 0.060044846 | 0.000768 | 0.001165 | 0.001155 |
| ZU | Actual | 1.71 | .35 | .53 | | | | | | |
| | M-1 | 1.7246 | 0.322574 | 0.515448 | -0.1946 | -0.072574 | -0.065448 | | | |
| | M-2 | 1.71922 | 0.32928 | 0.527736 | -0.18922 | -0.07928 | -0.077736 | | | |
| | M-3 | 1.72439 | 0.327158 | 0.511569 | -0.19439 | -0.077158 | -0.061569 | | | |
| | M-4 | 1.72074 | 0.317665 | 0.585691 | -0.19074 | -0.067665 | -0.055691 | | | |
| | M-5 | 1.72381 | 0.330562 | 0.49197 | -0.19381 | -0.070562 | -0.04197 | | | |
| | | | | | 0.183686257 | 0.068561956 | 0.061353375 | 0.001074 | 0.001959 | 0.001158 |
| CHC | Actual | 1.77 | .33 | .54 | | | | | | |
| | M-1 | 1.7686 | 0.311777 | 0.560264 | -0.2386 | -0.061777 | -0.110264 | | | |
| | M-2 | 1.79259 | 0.310986 | 0.541326 | -0.26259 | -0.060986 | -0.091326 | | | |
| | M-3 | 1.7898 | 0.314044 | 0.516528 | -0.2598 | -0.064044 | -0.066528 | | | |
| | M-4 | 1.78484 | 0.328276 | 0.538383 | -0.25484 | -0.078276 | -0.088383 | | | |
| | M-5 | 1.79116 | 0.315896 | 0.521153 | -0.26116 | -0.065896 | -0.071153 | | | |
| | | | | | 0.245040174 | 0.066842452 | 0.083229706 | 0.001384 | 0.002026 | 0.001541 |
| | | | | | | | % avg | 0.2% | 1.6% | 2.5% |

| error | | |
|---|---|---|
| Height (length) | Shoulder (length) | Arm (length) |
| 0.2% | 1.6% | 2.5% |

| accuracy | | |
|---|---|---|
| Height (length) | Shoulder (length) | Arm (length) |
| 99.8% | 98.4% | 97.5% |

FIG. 29A

| True measurement value used for height estimation | Height error (cm) |
|---|---|
| 2, 3, 4, 5, 6, 8, 9, 10, 11, 12, 13, 14, 15, 18 | 2.882 |
| 2, 3, 5, 6, 8, 9, 10, 11, 12, 13, 14, 15, 18 | 2.878 |
| 2, 3, 5, 6, 8, 9, 10, 11, 12, 13, 14, 15 | 2.886 |
| 3, 6, 8, 9, 10, 11, 12, 13, 14, 15 | 2.811 |
| 3, 6, 8, 9, 10, 13, 14, 15 | 3.070 |
| 3, 6, 8, 9, 13, 14, 15 | 3.146 |
| 6, 8, 9, 13, 14 | 3.220 |
| 6, 9, 13 | 3.275 |
| 6, 13 | 3.688 |
| 13 | 3.817 |

FIG. 29B

1 Height
2 Neck
3 Chest
4 Belly button waist
5 Gluteal hip
6 Neck shoulder elbow wrist
8 Across back shoulder neck
9 Neck to gluteal hip
10 Natural waist
11 Max. hip
12 Natural waist rise
13 Shoulder to mid-hand
14 Upper arm
15 Wrist
18 Max. thigh

BODY MEASUREMENT DEVICE AND METHOD FOR CONTROLLING THE SAME

CROSS-REFERENCE TO RELATED APPLICATION

Pursuant to 35 U.S.C. § 119, this application claims the benefit of U.S. Provisional Application No. 62/894,846, filed on Sep. 1, 2019, and claims the benefit of the earlier filing date and right of priority to International Application No. PCT/KR2020/000213, filed on Jan. 6, 2020, the contents of which are all hereby incorporated by reference herein in their entirety.

BACKGROUND

1. Field

The present disclosure relates to a body measurement device and a method for controlling the same, and more particularly, to a body measurement device and a method for controlling the same, in which a user's image is captured, a body line image and a skeleton image are acquired based on the captured image, and the user's body size is measured based on the acquired body line image and skeleton image.

2. Description of the Related Art

In purchasing clothes, a customer should know his or her exact body size. In particular, when purchasing clothes online, it is possible to try on clothes. Also, when purchasing clothes offline, it is difficult and inconvenient to try on the clothes due to a concern of a damage to the clothes or a delay in time.

Technologies commercialized among technologies developed to solve the problem are to use a 3D scanner or measure a body size by setting a plurality of digital cameras. However, these technologies have problems in that a specific place and an expensive equipment are required to allow consumers to be difficult to use the technologies.

Also, there is a limitation that a typical camera is capable of measuring a body size only when the user is naked or is in a tight-fit dress.

SUMMARY

An object of the present disclosure is to provide a body measurement device and a method for controlling the same, in which a user's image is captured, a body line image and a skeleton image are acquired based on the captured image, and the user's body size is measured based on the acquired body line image and skeleton image when the user takes a specific pose.

Other object of the present disclosure is to provide a body measurement device and a method for controlling the same, in which a body length is extracted from a body line image and a skeleton image, and a rear waist circumference length is determined by multiplying a specific parameter by a body length.

Still another object of the present disclosure is to obtain an accurate body size through a correction when a body of a user in a loose-fit dress is measured, that is, when noise due to hair, clothes, or shoes is included in a captured image.

In addition to the objects of the present disclosure as mentioned above, additional objects and features of the present disclosure will be clearly understood by those skilled in the art from the following description of the present disclosure.

According to an aspect, there is provided a body measurement device including a camera configured to capture an image that includes an RGB image and a depth image, a display, and a controller configured to acquire a source image that includes a skeleton image and a body line image of a user based on the captured image, acquire a body size including a body height based on the source image, and control the display to display the body size.

According to another aspect, there is also provided a method for controlling a body measurement device, the method including capturing an image that includes an RGB image and a depth image, acquiring a source image that includes a skeleton image and a body line image of a user based on the captured image, acquiring a body size including a body height based on the source image, and controlling a display to display the body size.

According to one embodiment of the present disclosure, if the user takes a specific pose, the user's image is captured, and a body line image and a skeleton image are acquired from the captured image. Since the user's body size may be measured based on the acquired body line image, the user's image may be captured by a simple operation and an exact body size may be measured.

According to another embodiment of the present disclosure, a skeleton image is extracted from the captured image, and the skeleton image, an RGB image and a depth image may be combined with one another to acquire the user's body line image. Therefore, the user's body size may be measured more exactly.

According to still another embodiment of the present disclosure, a first length may be extracted from a body line image, and a specific parameter may be multiplied by the first length to determine a rear waist circumference length. Therefore, a waist circumference length which is invisible from a front image may exactly be measured.

According to yet another embodiment of the present disclosure, even when a body height including a user's hair volume is measured, it is possible to acquire an accurate body height by correcting the measured body height.

According to further another embodiment of the present disclosure, even when an image of a user wearing shoes is captured, it is possible to acquire an accurate body height through a correction.

According to still another embodiment of the present disclosure, even when an image of a user wearing loose-fit clothes is captured, it is possible to acquire accurate circumference values through a correction.

In addition to the effects of the present disclosure as mentioned above, additional effects and features of the present disclosure will be clearly understood by those skilled in the art from the following description of the present disclosure.

BRIEF DESCRIPTION OF THE DRAWINGS

The above and other aspects, features, and advantages of certain embodiments will be more apparent from the following detailed description taken in conjunction with the accompanying drawings, in which:

FIG. 6A and FIG. 6B illustrate input images according to one embodiment of the present disclosure;

FIG. 17A and FIG. 17B illustrate that a front waist circumference length, a side waist circumference length, and a rear waist circumference length are measured according to one embodiment of the present disclosure;

FIG. 18 illustrates data of a user's actual height and a measured height according to one embodiment of the present disclosure;

FIG. 19 illustrates data of a user's actual bust circumference length and a measured bust circumference length according to one embodiment of the present disclosure;

FIG. 20 illustrates data of a user's actual underbust circumference length and a measured underbust circumference length according to one embodiment of the present disclosure;

FIG. 21 illustrates data of a user's actual waist circumference length and a measured waist circumference length according to one embodiment of the present disclosure;

FIG. 22 illustrates data of a user's actual hip circumference length and a measured hip circumference length according to one embodiment of the present disclosure;

FIG. 23 illustrates data of an error and exactness of user's body size measurement data according to one embodiment of the present disclosure;

FIG. 24 illustrates data of an error and exactness of user's body size measurement data according to one embodiment of the present disclosure;

FIG. 29A and FIG. 29B illustrate experimental values of body height estimation according to one embodiment of the present disclosure;

DETAILED DESCRIPTION

Reference will now be made in detail to the preferred embodiments of the present specification, examples of which are illustrated in the accompanying drawings. Wherever possible, the same reference numbers will be used throughout the drawings to refer to the same or like parts. The suffixes "module" and "unit" for the elements used in the following description are given or used in common by considering facilitation in writing this disclosure only but fail to have meanings or roles discriminated from each other.

Also, in description of the embodiments disclosed in this specification, if detailed description of the disclosure known in respect of the present disclosure is determined to make the subject matter of the embodiments disclosed in this specification obscure, the detailed description will be omitted.

Also, the accompanying drawings are only intended to facilitate understanding of the embodiments disclosed in this specification, and it is to be understood that technical spirits disclosed in this specification are not limited by the accompanying drawings and the accompanying drawings include all modifications, equivalents or replacements included in technical spirits and technical scope of the present disclosure.

Although the terms such as "first" and/or "second" in this specification may be used to describe various elements, it is to be understood that the elements are not limited by such terms. The terms may be used to identify one element from another element.

The expression that an element is "connected" or "coupled" to another element should be understood that the element may directly be connected or coupled to another element, a third element may be interposed between the corresponding elements, or the corresponding elements may be connected or coupled to each other through a third element. On the other hand, the expression that an element is "directly connected" or "directly coupled" to another element" means that no third element exists therebetween.

It is to be understood that the singular expression used in this specification includes the plural expression unless defined differently on the context.

In this application, it is to be understood that the terms such as "include" and "has" are intended to designate that features, numbers, steps, operations, elements, parts, or their combination, which are disclosed in the specification, exist, and are intended not to previously exclude the presence or optional possibility of one or more other features, numbers, steps, operations, elements, parts, or their combinations.

Figure 1:
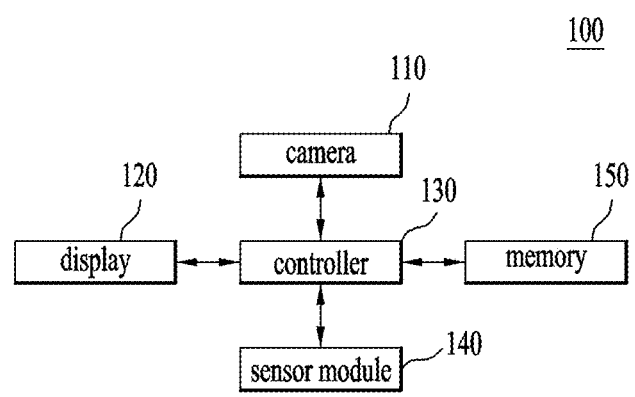
FIG. 1 is a block diagram illustrating a body measurement device according to one embodiment of the present disclosure.

FIG. 1 is a schematic view illustrating a body measurement device according to one embodiment of the present disclosure.

Referring to FIG. 1, the body measurement device 100 includes a camera 110, a display 120, a controller 130, a sensor module 140, and a memory 150.

The camera 110 captures a first image that includes an RGB image and a depth image. The camera 110 includes a depth camera 110 capable of capturing a depth image, an RGB camera capable of acquiring an RGB color image, and an IR camera capable of making a depth image.

The depth camera 100 includes an SL camera. The SL camera is a camera based on structure light (SL), and radiates a signal of a specific pattern and calculates the depth by analyzing a changed level of a pattern in accordance with an object surface. For example, if the SL camera is operated, an infrared pattern of 30000 dots is scanned on a face from a component such as a dot projector. This pattern is again reflected toward the infrared camera without distortion if scanned on a plane space such as a desk. However, since a face of a person is not a plane, it has many flections in accordance with a position and a size of eyes, a nose and lips. Therefore, light generated from the dot projector is reflected toward the face and therefore distortion of a certain pattern is formed. The SL type camera recognizes a user by reading out a change of this pattern.

The depth image means an image that includes a depth map. The depth map means an image having information related to a distance from a viewpoint to an object surface in a 3D computer graphic.

The camera 110 includes a depth camera and an RGB camera. Also, the camera 110 may include a depth camera and an RGB camera individually. The camera 110 may include at least one depth camera and at least one RGB camera.

The display 120 displays a graphic image in accordance with a control command from the controller 130.

The controller 130 estimates a user's pose based on a first image, and if the user's pose is a first pose, the controller 130 controls the camera 110 to capture a second image that includes a user's body image in front of the camera 110, acquires the user's body line image based on the captured second image, measures the user's body size based on the acquired body line size, and controls the display 120 to display the user's body size.

The controller 130 may be implemented in a physical form, for example, a chipset. The controller 130 may be implemented as a single chipset or may be implemented as a plurality of chipsets. The controller 130 may serve as a processor and, for example, may be a system on chip (SOC) or an application processor.

The sensor module 140 senses a distance with a user in accordance with the control command from the controller 130.

The memory 150 stores the first image and the second image in accordance with the control command from the controller 130.

Figure 2:
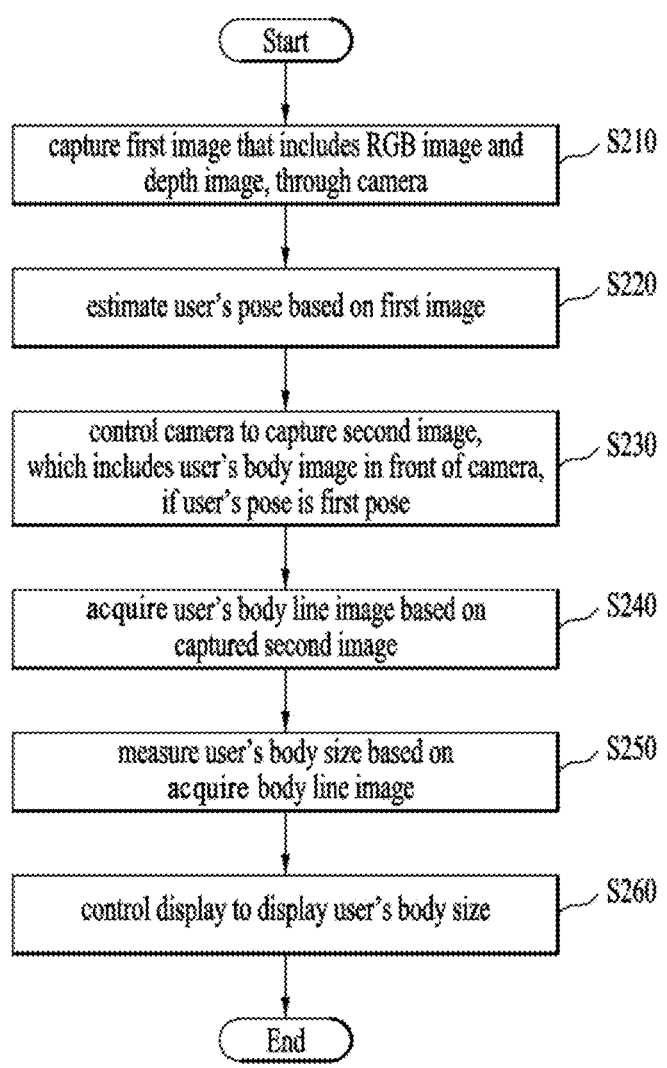
FIG. 2 is a flow chart illustrating a method for controlling a body measurement device according to one embodiment of the present disclosure.

FIG. 2 is a flow chart illustrating a method for controlling a body measurement device according to one embodiment of the present disclosure.

Referring to FIG. 2, a first image that includes an RGB image and a depth image is captured through the camera 110 (S210).

A user's pose is estimated based on the first image (S220).

If the user's pose is a first pose, the camera 110 is controlled to capture a second image that includes the user's body image in front of the camera 110 (S230).

The user's body line image is acquired based on the captured second image (S240). According to one embodiment of the present disclosure, the controller 130 extracts a skeleton image based on the first image.

The user's body size is measured based on the acquired body line image (S250). Also, the controller 130 may measure a body size based on the body line image and the skeleton image.

The controller 130 controls the display 120 to display the user's body size (S260).

Figure 3:
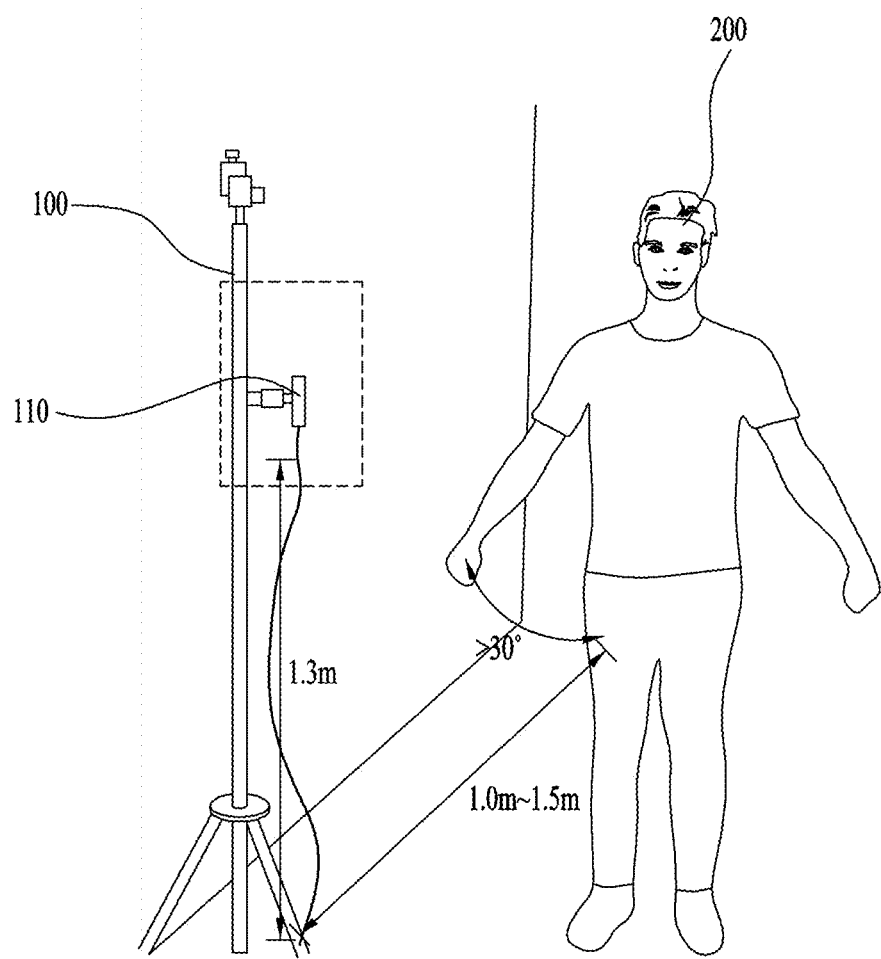
FIG. 3 illustrates that a user stands in front of a body measurement device according to one embodiment of the present disclosure.

FIG. 3 illustrates that a user stands in front of a body measurement device according to one embodiment of the present disclosure.

Referring to FIG. 3, a user 200 stands in front of the body measurement device 100. In this case, the camera 110 includes a depth camera.

First of all, a position of the camera 110 will be described.

Since the user's leg portion is not captured by the camera 110, it is set to a fixed value to measure the user's height. The position of the camera 110 is changed depending on a range (140 cm to 200 cm in case of height) of a range to be measured. A distance between the camera 110 and the user 200 is determined considering a size of a target to be measured and a field of view (FOV) of the camera 110. The distance is determined considering exactness of a distance value of the depth camera 110. That is, it is important to select a position having high exactness, and exactness of a depth is reduced when the distance between the camera 110 and the user 200 is too short or long.

The position of the camera 110 may be 1.3 m from the ground.

The distance between the camera 110 and the user may range from 1.0 m to 1.5 m.

Resolution of the camera 110 will be described. The higher resolution of the camera 110 is, the higher exactness of a meter per pixel (MPP) is, whereby measurement may be performed more exactly.

An input image of the camera 110 will be described.

The input image may be i) a depth image, ii) a depth image and a RGB image, or iii) a depth image and an IR image.

In case of the depth image, the controller 130 may acquire distance and length information for body measurement from the depth image. If there are no additional RGB image and IR raw image, the controller 130 may extract a skeleton image from the depth image.

In case of the RGB image and the IR raw image, the controller 130 extracts a pose for automatic capturing from the RGB image and the IR raw image.

Also, the RGB image and the IR raw image may be used for additional application. For example, the controller 130 may execute gender recognition through face recognition, weight prediction through deep-learning or weight prediction algorithm and rear circumference prediction (when the user's front image is only captured) through deep-learning, based on the RGB image and the IR raw image.

Also, the controller 130 may improve exactness by executing a fusion algorithm based on information obtained from the depth camera and information using deep learning having an RGB image and an IR-raw image as inputs.

Figure 4:
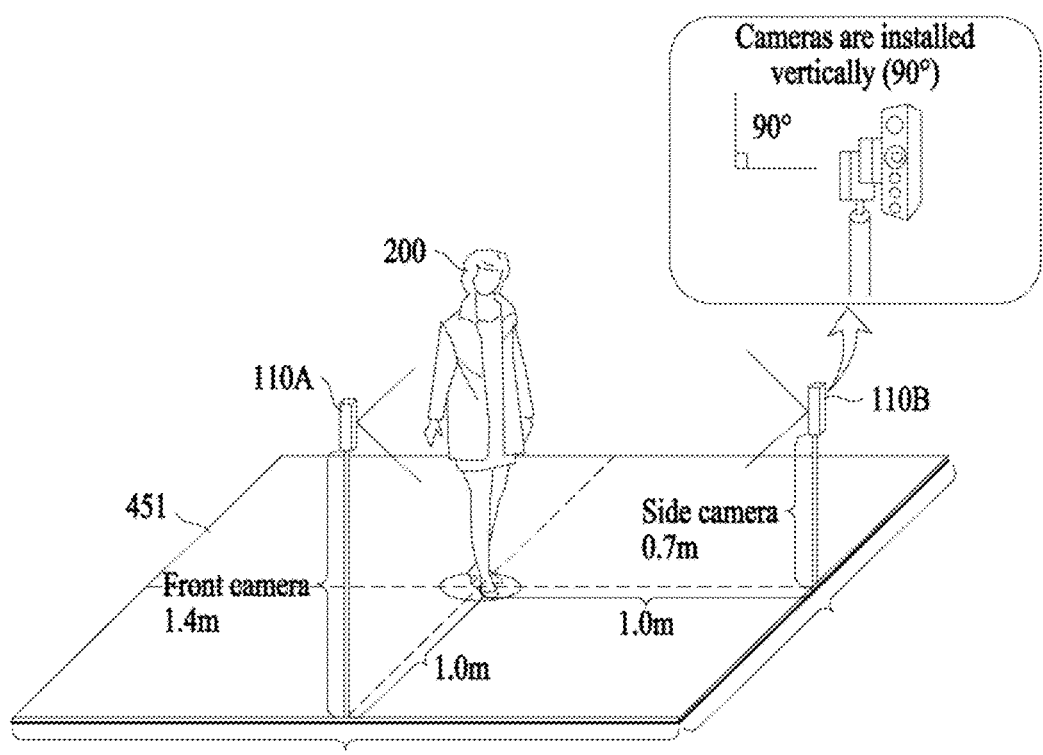
FIG. 4 illustrates that a user stands in front of a body measurement device according to one embodiment of the present disclosure.

FIG. 4 illustrates that a user stands in front of a body measurement device according to one embodiment of the present disclosure.

Unlike the embodiment of FIG. 3, a plurality of cameras may be used to capture images of a user at a plurality of angles. When two cameras are used to capture images of the user, one of the two cameras may be disposed to capture a front image of the user and the other may be disposed to capture a side image of the user.

A distance from a camera to the user may be set similar to the case of FIG. 3. Desirably, two cameras and the user may be located in a space of "2.0 m×2.0 m" or a space of "3.0 m×3.0 m."

A front camera may be located at a height of about 1.4 m from the ground. A side camera may be located at a height of about 0.7 m from the ground. A reason for such difference in height between the two cameras is that the user is photographed upright vertically, so a plurality of images spaced apart in a longitudinal direction helps to obtain accurate information.

Figure 5:
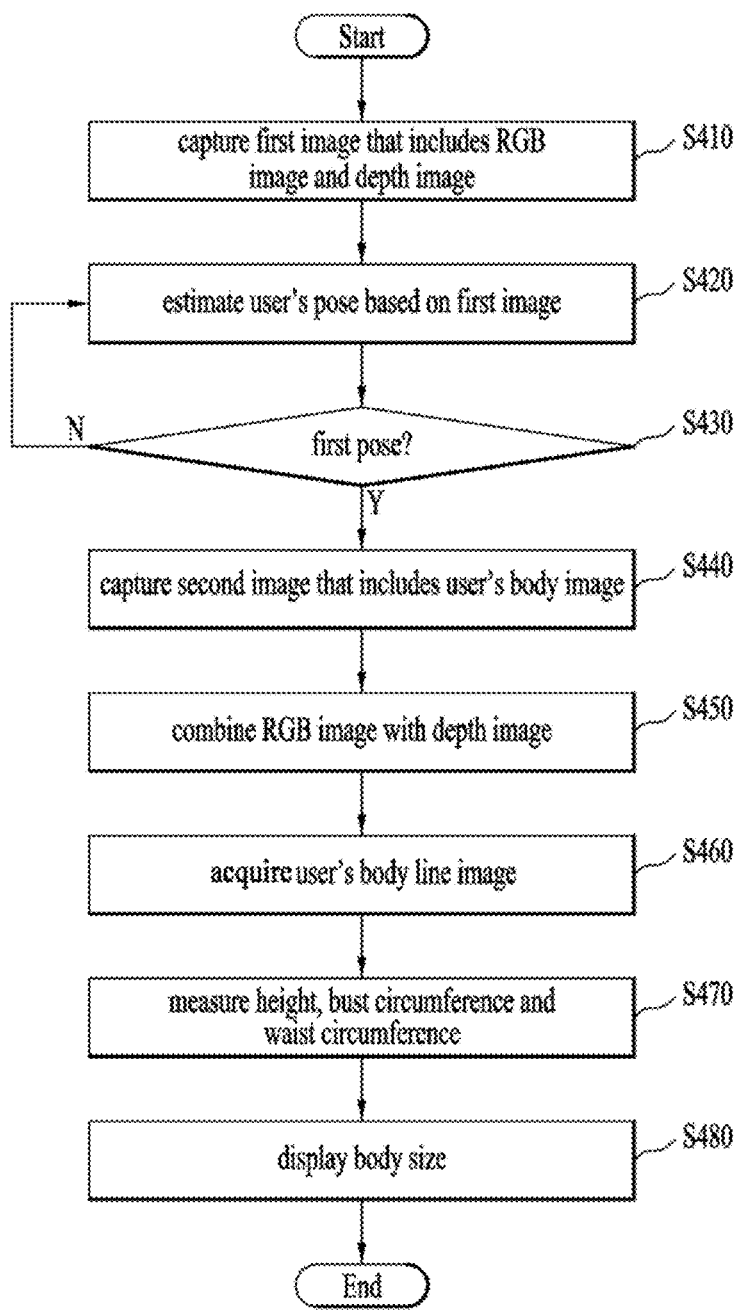
FIG. 5 is a flow chart illustrating a method for controlling a body measurement device according to one embodiment of the present disclosure.

FIG. 5 is a flow chart illustrating a method for controlling a body measurement device according to one embodiment of the present disclosure. The present disclosure is performed by the controller 130.

Referring to FIG. 5, a first image that includes a depth image and an RGB image is captured (S410).

A user's pose is estimated based on the first image (S420).

If the user's pose is a first pose (S430), the camera 110 captures a second image that includes the user's body image (S440). The controller 130 controls the camera 110 to capture an image or continuously capture images. In this case, the first pose may be one pose or a plurality of poses. If the first pose becomes a plurality of poses, it is advantageous that measurement exactness in a body size may be improved.

If the user's pose is not a first pose (S440), the user's pose is again estimated based on the first image (S420). The controller 130 measures a slope corresponding to the user's pose through the sensor module 140, and if the user's pose is more inclined than the first pose toward a left or right direction at a predetermined range or more, the controller 130 displays a warning message on the screen. The controller 130 may control a speaker (not shown) to output a voice message "a pose is inclined toward a right side. So, please stand straight".

According to the present disclosure, if the user's pose is more inclined than the first pose, the warning message is displayed to allow the user to take a right pose, whereby an exact body size may be measured.

The RGB image and the depth image are combined with each other (S450).

The body line image is acquired based on the RGB image and the depth image (S460). According to one embodiment of the present disclosure, the controller 130 may acquire a body line image and a skeleton image based on the RGB image and the depth image.

A height, a bust circumference, and a waist circumference are measured based on the body line image (S470).

The measured body size is displayed (S480).

FIG. 6A and FIG. 6B illustrate input images according to one embodiment of the present disclosure.

FIG. 6A means the RGB image of the input images.

The RGB image means an image to which an RGB mode is applied. The RGB model is the most basic color model, and considers a color as a combination of three components of red, green and blue. In the RGB model, a black color is expressed as R=G=B=0, a white color is expressed as R=G=B=255, a red color is expressed as R=255, G=B=0, and a yellow color is expressed as R=G=255, B=0. A case of R=G=B corresponds to a gray color which is an achromatic color.

Since each of R, G and B may have a value between 0 and 255, if the RGB model is used, a total of 256×256×256=16,777,216 colors may be expressed.

FIG. 6B means a depth image of the input images.

The depth image means an image obtained by capturing same scenes at different angles to acquire a depth map. The depth map means an image indicating a relative distance of pixels existing in the image by categorizing the relative distance in a gray scale. In case of the depth map, a close portion is indicated by bright pixels, and a remote portion is indicated by dark pixels.

Figure 7A:
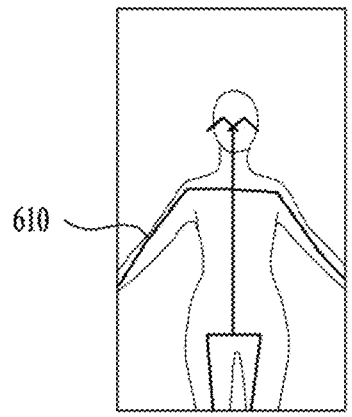
FIG. 7A, FIG. 7B and FIG. 7C illustrate that a body line image is acquired in accordance with one embodiment of the present disclosure.
Figure 7B:
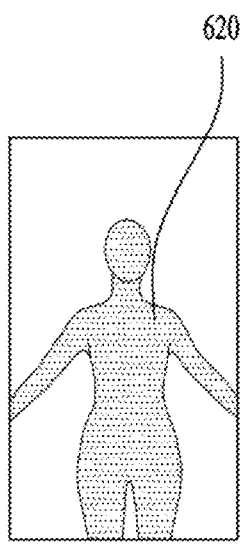
Figure 7C:
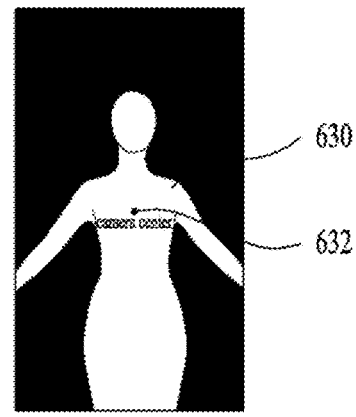

FIG. 7A, FIG. 7B and FIG. 7C illustrate that a body line image is acquired in accordance with one embodiment of the present disclosure.

FIG. 7A illustrates a skeleton image extracted from a second image. FIG. 7B illustrates an image obtained by combining an RGB image and a depth image. FIG. 7C illustrates a user's body line image.

Referring to FIG. 7A, the controller 130 extracts a skeleton image 610 based on the second image.

Referring to FIG. 7B, the controller 130 acquires a combined image 620 by combining the RGB image with the depth image.

Referring to FIG. 7C, the controller 130 acquires the user's body line image 630 by combining the extracted skeleton image 610, the RGB image and the depth image 620 with one another.

The controller 130 measures the user's height based on a camera center 632. A detailed description of this case will be given with reference to FIG. 14.

Figure 8:
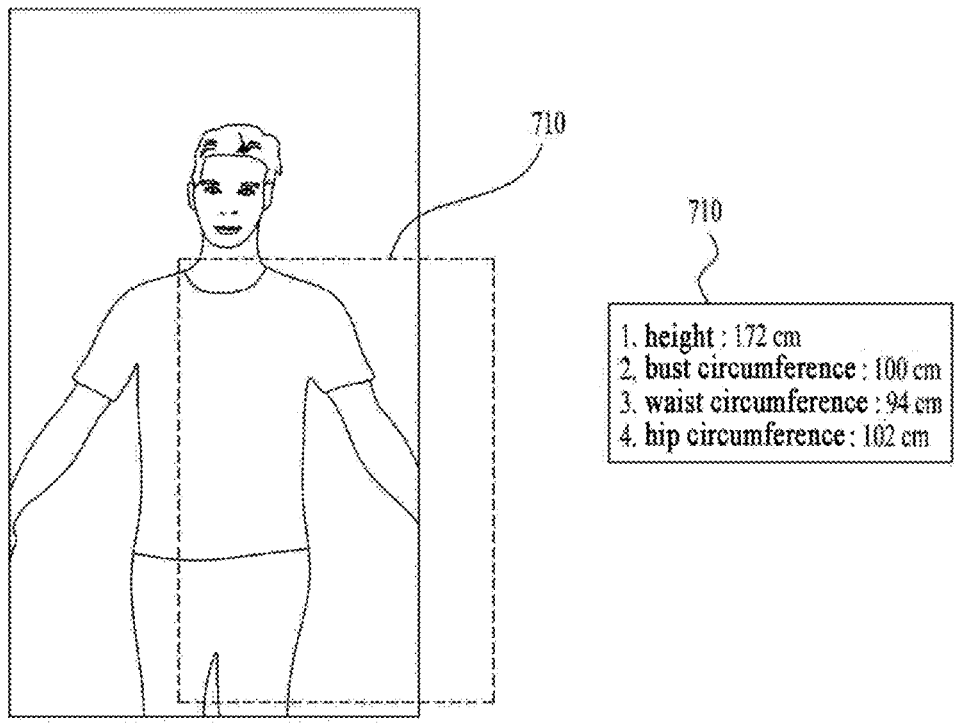
FIG. 8 illustrates a user's body size measurement result according to one embodiment of the present disclosure.

FIG. 8 illustrates that a user's body size measurement result according to one embodiment of the present disclosure.

Referring to FIG. 8, the controller 130 displays the user's body size measurement result on the screen.

For example, the body size measurement result includes a height 71, a bust circumference 72, a waist circumference 73, a hip circumference 74. The height 71 may be 172 cm, the bust circumference 72 may be 100 cm, the waist circumference 73 may be 94 cm, and the hip circumference may be 102 cm.

Figure 9:
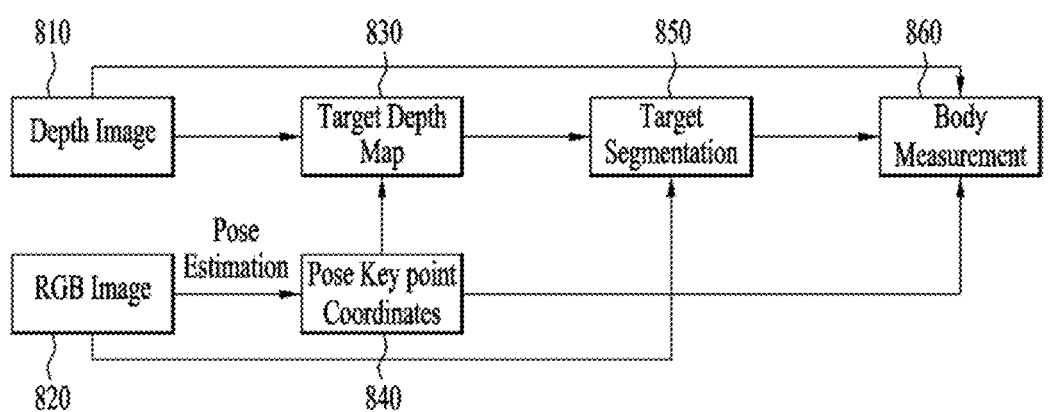
FIG. 9 illustrates a body measurement algorithm according to one embodiment of the present disclosure.

FIG. 9 illustrates a body measurement algorithm according to one embodiment of the present disclosure.

Referring to FIG. 9, a depth image 810 and an RGB image 820 are received as input images.

The controller 130 estimates the user's pose based on the RGB image 820, and acquires a pose key point coordinate 840.

The controller 130 acquires a target depth map 830 based on the depth image 810 and the pose key point coordinate 840.

The controller 130 acquires a target segmentation image 850 based on the target depth map 830 and the RGB image 820.

The controller 130 executes body size measurement 860 based on the target segmentation image 850.

The controller 130 may measure a height, a bust circumference length, an underbust circumference length, a waist circumference length, and a hip circumference length as body size measurement of a target.

Figure 10A:
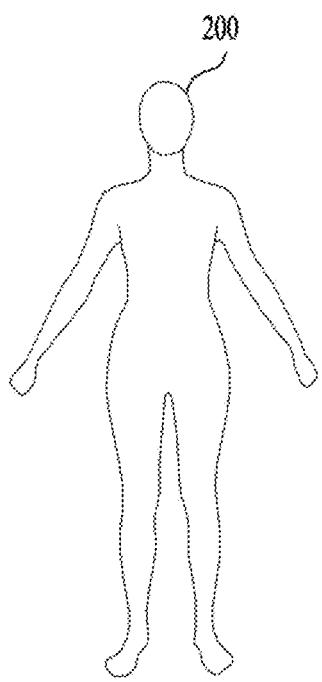
FIG. 10A and FIG. 10B illustrate a user's pose according to one embodiment of the present disclosure.
Figure 10B:
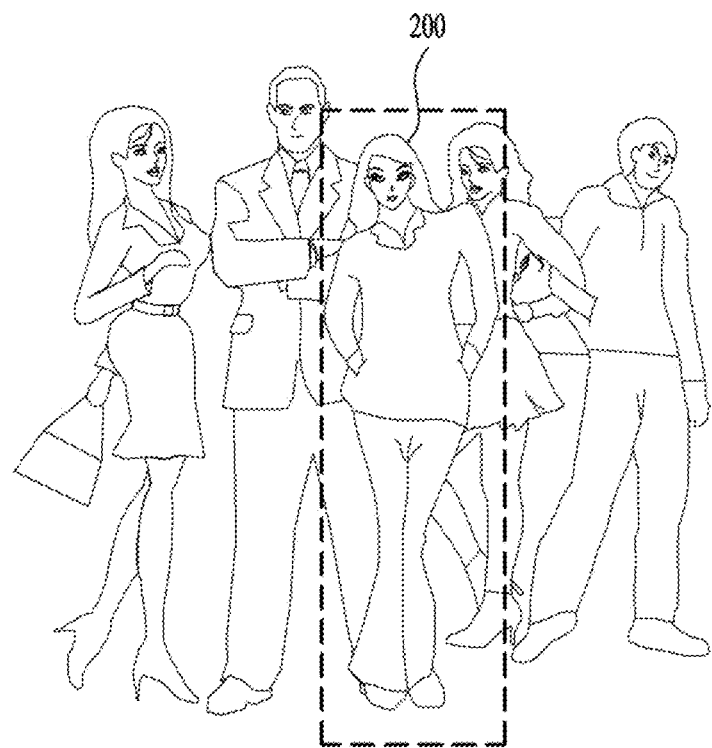

FIG. 10A and FIG. 10B illustrates a user's pose according to one embodiment of the present disclosure.

FIG. 10A illustrates a user's pose. Referring to FIG. 9A, the controller 130 estimates the user's pose based on an ear image, a nose image, an eye image, a shoulder image, a tiptoe image and a hip image, which are included in the RGB image 200.

The controller 130 controls the camera 110 to automatically capture a second image, which includes the user's body image in front of the camera 110, if the user's pose is a first pose. In this case, the first pose may be a key pose for executing a measurement algorithm.

The key pose may be defined as follows. In this pose, the user looks at the camera while standing at attention, and spreads out his/her arms at a specific angle. In this case, the specific angle may be 30 degrees. The key pose may have various poses without being limited to one pose.

If the user takes a key pose, the camera captures a plurality of user front images. This is because that data area accumulated to lower an error rate than that of one image if the plurality of user front images are captured.

The key pose may be checked from a key point of a pose. For example, when the user stands in front of the camera, the key point may be ankles, elbows, ears, eyes, a nose, a neck, shoulders, hips, etc.

FIG. 10B illustrates a method for specifying a user whose body size will be measured if there are a plurality of users.

Referring to FIG. 10B, the sensor module 140 senses a distance between the body measurement device 100 and a user.

If there are plurality of users, the controller 130 controls the sensor module 140 to sense a user 200 closest to the body measurement device 100 among the plurality of users, and if the user's pose is a first pose, controls the camera 110 to capture a second image that includes a body image of the user 200 in front of the camera 110. If a plurality of second images are captured, the controller 130 independently measures a body size based on the second image. Therefore, in the present disclosure, it is advantageous that an error rate may be lowered.

Figure 11:
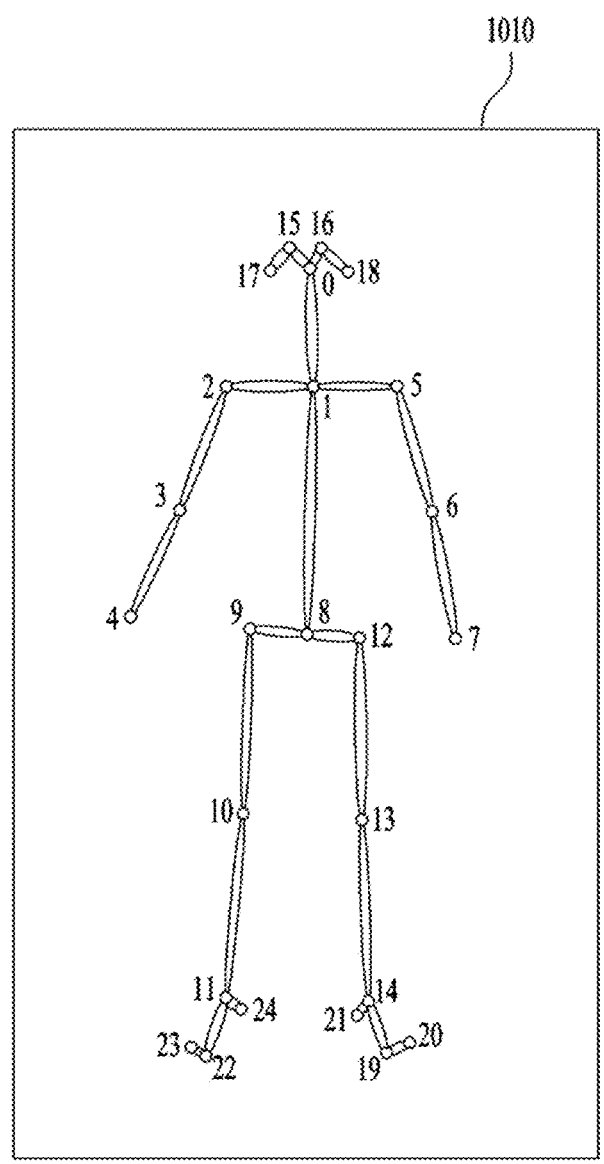
FIG. 11 illustrates a skeleton image according to one embodiment of the present disclosure.

FIG. 11 illustrates a skeleton image according to one embodiment of the present disclosure.

Referring to FIG. 11, the controller 130 extracts a skeleton image 1010 based on the first image, and estimates the user's pose based on the extracted skeleton image 1010.

The controller 130 may estimate the user's pose by using pose key points. The key points may be ears 17 and 18, eyes 15 and 16, a nose 0, a neck from 0 to 1, shoulders 2 and 5, elbows 3 and 6, and hips 9 and 12. The key points may be used to identify a key pose, and may also be used to estimate a body measurement size.

The controller 180 may estimate the user's pose based on the skeleton image 1010. Also, the controller 180 may measure an arm length, a leg length, a waist circumference length, a bust circumference length, and a hip circumference length.

Figure 12:
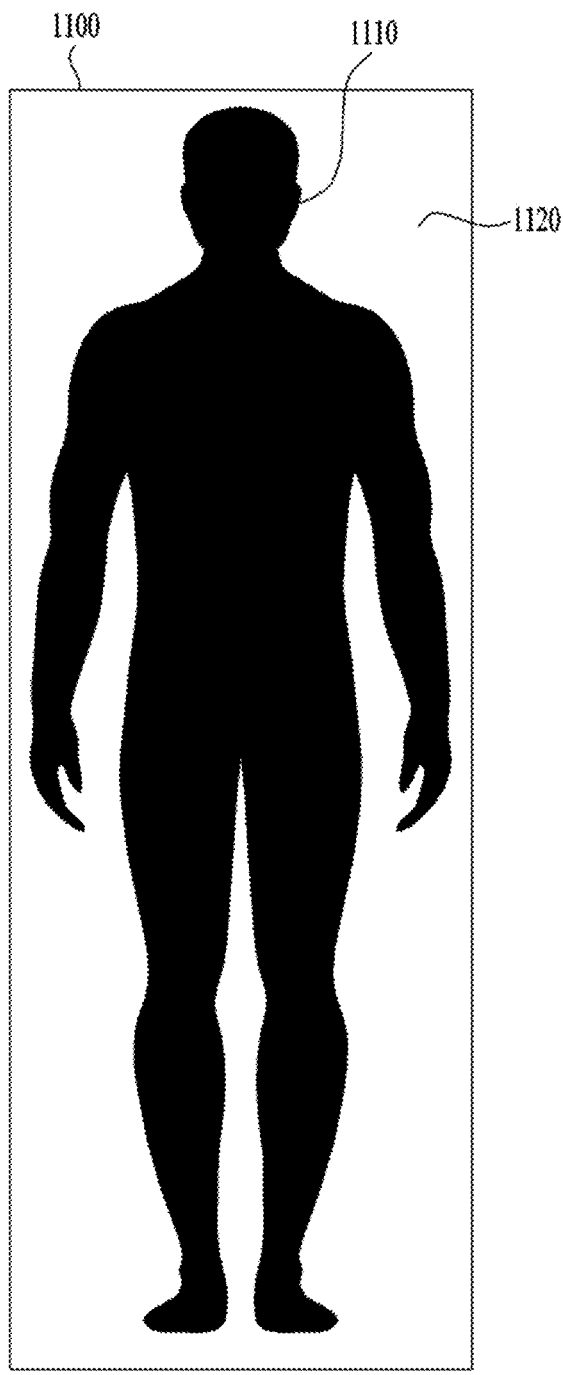
FIG. 12 illustrates that target segmentation is performed using an RGB image and a depth image according to one embodiment of the present disclosure.

FIG. 12 illustrates that target segmentation is performed using an RGB image and a depth image in accordance with one embodiment of the present disclosure.

Referring to FIG. 12, target segmentation is executed using the RGB image and the depth image.

Target segmentation is executed as follows.

The controller 130 combines the RGB image with the depth image, and acquires a body line image based on the combined RGB image and depth image. This will be described in more detail.

First of all, the controller 130 filters a depth map guided by the RGB image. The depth image includes a depth map.

The controller 130 executes trimap generation from the depth map. The controller performs matting for the depth map.

An output of target segmentation will be described.

The controller 130 acquires a segmentation map of a target subject. Next, the controller 130 removes noise for the segmentation map, and performs a smooth treatment of an edge portion.

According to the present disclosure, the segmentation map may be used as a guide for body size measurement.

The target segmentation map will be described.

As shown in FIG. 12, the body line image may be segmented into a black area 1110 and a white area 1120. The controller 130 considers the black area 1110 as a front view and arranges the black area 1110 at the front, and considers the white area 1120 as a background and arranges the white area 1120 behind the black area 1120. In this image, the black area 1110 may mean a character in which a user is interested, and the white area 1120 may mean a background behind the character.

Therefore, the controller 130 acquires the user's body line image 1100 based on the captured second image.

Figure 13:
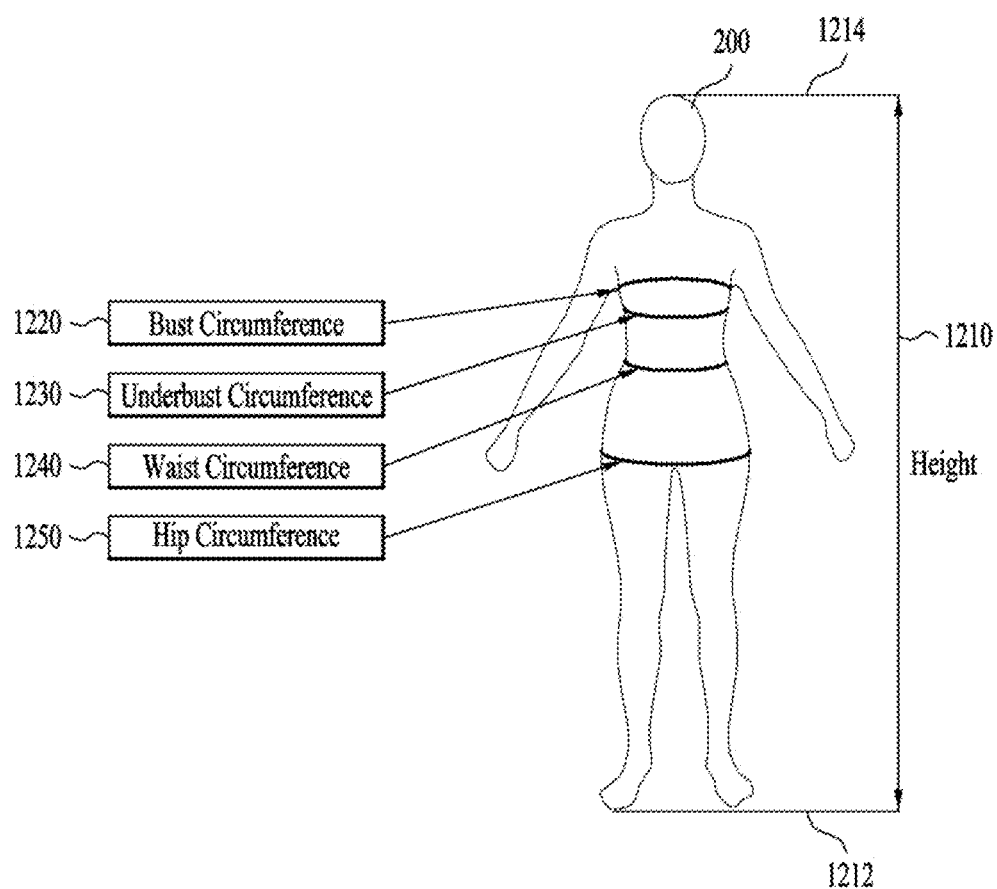
FIG. 13 illustrates a body size measurement target according to an example embodiment of the present disclosure.

FIG. 13 illustrates a body size measurement target according to one embodiment of the present disclosure.

Referring to FIG. 13, a height 1210, a bust circumference length 1220, an underbust circumference length 1230, a waist circumference length 1240, and a hip circumference length 1250 may be measured based on the body line image 1200.

In detail, following data are required when a body size is measured. A depth map, a pose key point coordinate, and a body segmentation mask are required. The controller 130 acquires a body line image 1200 based on the depth map, the pose key point coordinate and the body line mask.

Next, a body line measurement target is as follows. The controller 130 measures at least one of the user's height 1210, an arm length, a leg length, a bust circumference length 1220, a waist circumference length 1240, and a hip circumference length 1250.

The measurement portions may be measured based on the outline of the body line image 1200. Also, in case of the length corresponding to two points, for example, an arm length and a leg length may be measured.

Next, segmentation of body proportions and determination of a bust and a waist will be described.

The controller 130 segments the body line image 1200 into a predetermined ratio, determines a protruded portion of the body line image 1200 as a bust, and determines a recessed portion of the body line image 1200 as a waist.

For example, the height 1210 means a distance from the ground 1210 to a head end 1214.

A range between a neck and hips of the body line image 1200 is mainly used for body measurement. This portion may be considered as [0,1] in an upper body portion. The upper body portion includes a bust, a waist, and a hip portion. That is, when the body line image is divided into a predetermined ratio, a neck means 0, and the hip means 1.

The bust portion means a portion of [0.15 to 0.25] in the upper body.

The underbust portion means a portion of [0.35 to 0.45] in the upper body.

The waist portion means a portion of [0.65 to 0.75] in the upper body.

The hip portion means a portion of [0.95 to 1.00] in the upper body.

The above values are not fixed, and the controller 130 may set the values differently depending on the body line image with reference to the memory 150. The memory 150 includes various body line images, and stores a body proportion corresponding to each body line image.

Figure 14:
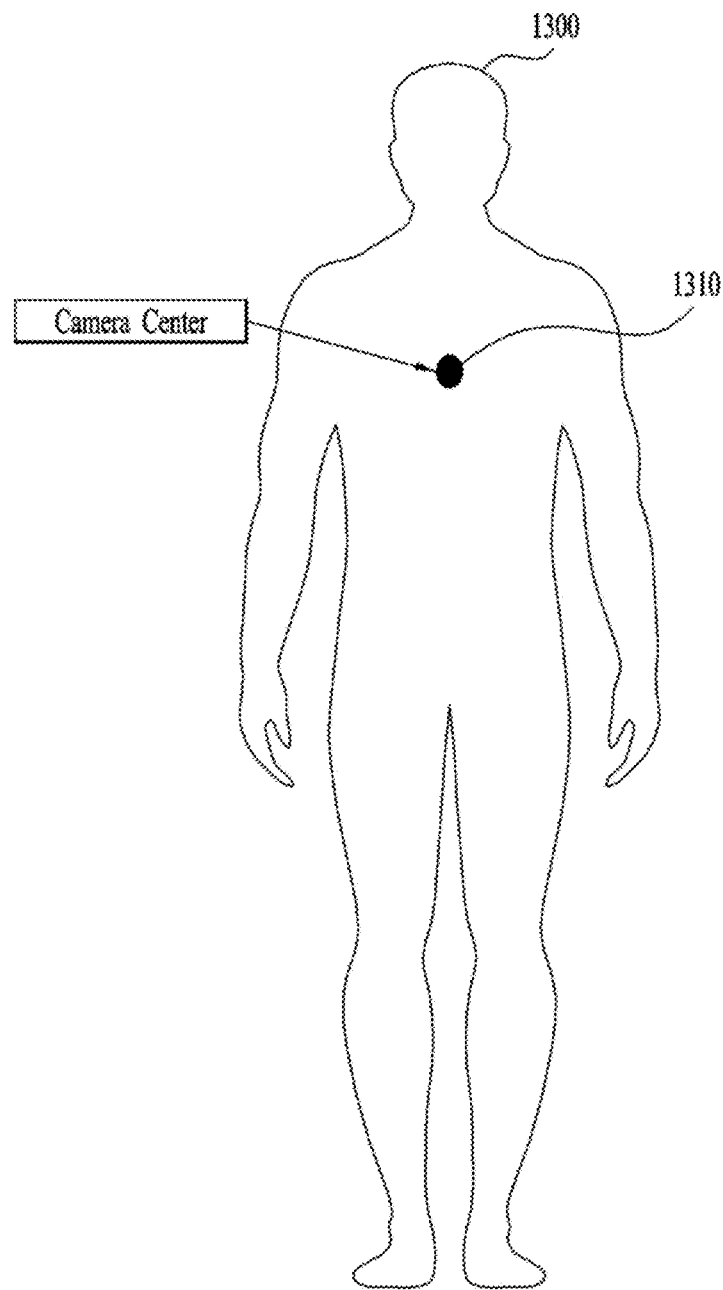
FIG. 14 illustrates that a user's height is measured according to one embodiment of the present disclosure.

FIG. 14 illustrates that a user's height is measured in accordance with one embodiment of the present disclosure.

Referring to FIG. 14, a body line image 1300 includes a camera center 1310. The controller 130 may measure the user's height by using the camera center 1310.

The camera center 1310 is a distance from the ground to a camera lens, and means a camera height.

For example, if the camera height is 175 cm, the controller 130 controls the sensor module 140 to measure the camera height. The controller 130 measures the user's height based on the camera height.

If the camera height is lower than the user's height, the controller 130 determines a value obtained by adding a) the camera height to b) a distance between the camera and the user's head as the user's height.

For example, if the camera height is 175 cm and the distance between the camera and the user's head is 5 cm, the controller 130 determines 180 cm obtained by adding 175 cm to 5 cm as the user's height.

If the camera height is higher than the user's height, the controller 130 determines a value obtained by subtracting b) a distance between the camera and the user's head from a) the camera height as the user's height.

For example, if the camera height is 175 cm and the distance between the camera and the user's head is 5 cm, the controller 130 determines 170 cm obtained by subtracting 5 cm from 175 cm as the user's height.

Figure 15:
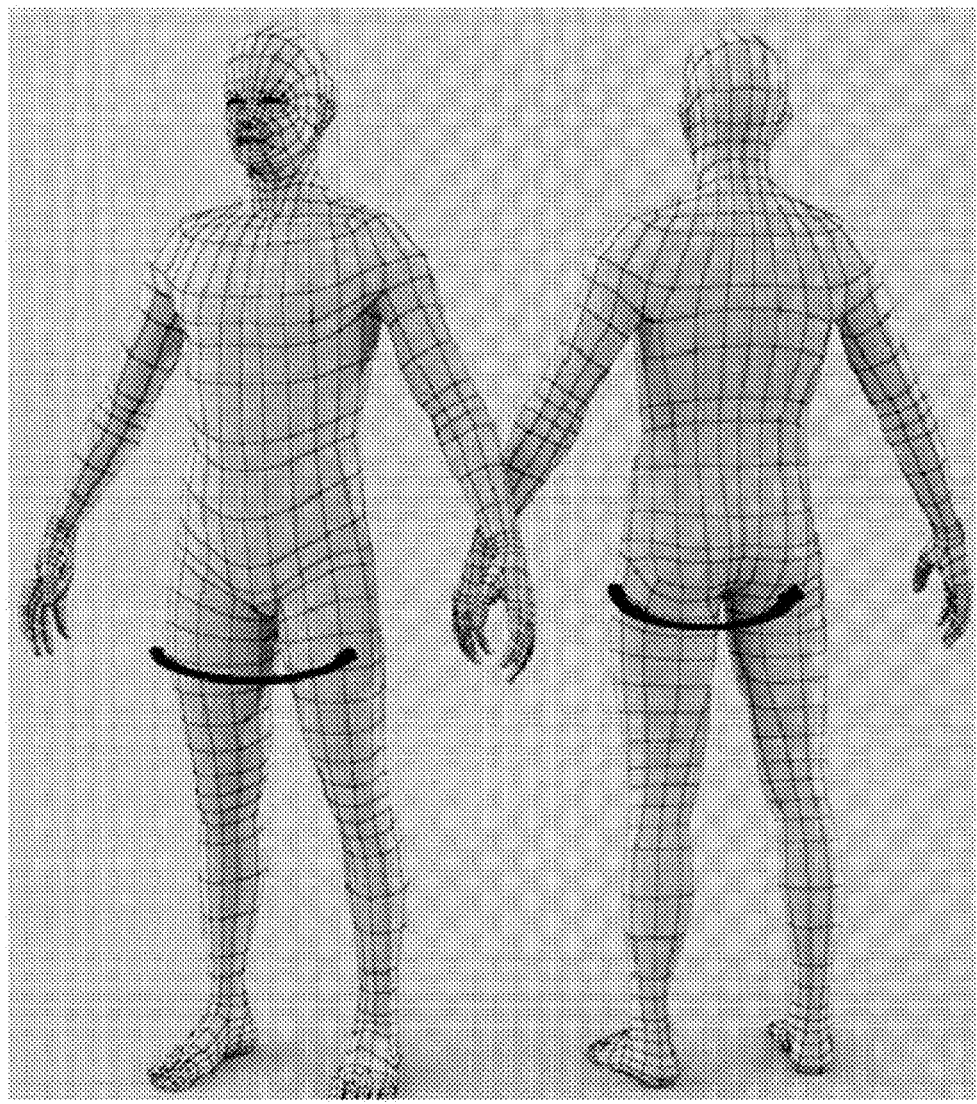
FIG. 15 illustrates two methods for measuring a user's waist circumference length according to one embodiment of the present disclosure.

FIG. 15 illustrates two methods for measuring a user's waist circumference length in accordance with one embodiment of the present disclosure.

FIG. 15 illustrate that a user's front and rear images are captured.

The first method is the case that both a front image and a rear image are captured. In this case, the controller 130 may most exactly measure a circumference length based on the depth map. Also, since a ratio of a body size and depth information may be known based on the skeleton image, the controller 130 may measure the circumference length more exactly.

The second method is the case that a front image is only captured. A rear circumference length may be obtained using an estimation method. That is, the rear circumference length is associated with a straight line length of the body. The rear circumference length may be obtained by multiplying a specific parameter by a straight line length based on experimental data.

This will be described later in detail with reference to FIG. 16A, FIG. 16B, FIG. 17A and FIG. 17B.

Figure 16A:
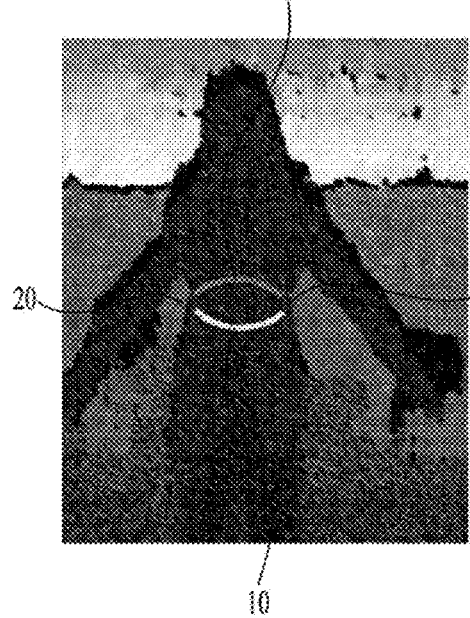
FIG. 16A and FIG. 16B illustrate that a waist circumference length is measured according to one embodiment of the present disclosure.
Figure 16B:
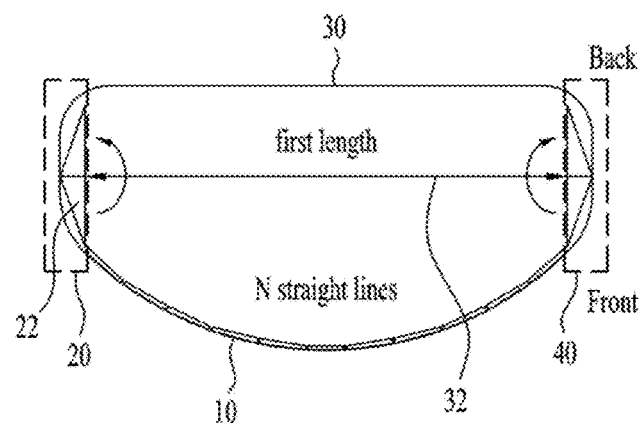

FIG. 16A and FIG. 16B illustrates that a waist circumference length is measured in accordance with one embodiment of the present disclosure.

In the present disclosure, a description will be given based on that the waist circumference length is measured as an example. However, a bust circumference length and a hip circumference length may be measured in the same method.

FIG. 16A illustrates a user's waist circumference length area in a full user body line image. FIG. 16B illustrates a user's waist circumference length area in detail.

Referring to FIG. 16A, the waist circumference length 1510 is equal to front waist circumference length 10+side waist circumference lengths 20 and 40+rear waist circumference length 30.

As shown in FIG. 16B, an enlarged image that includes the front waist circumference length 10, the side waist circumference lengths 20 and 40 and the rear waist circumference length 30 will be described.

In case of the front waist circumference length 10, the controller 130 obtains the front waist circumference length 10 by segmenting the front waist circumference into n straight lines and adding n straight line lengths.

The controller 130 uses data having noise of a predetermined range or more among data acquired from the depth camera for calculation of the side waist circumference length 20. The controller 130 uses data having noise less than a predetermined range for calculation of the front waist circumference length 10.

In the present disclosure, since the data having noise less than a predetermined range are explicit data, the data may be used for measurement of the front waist circumference length. Since the data having noise of a predetermined range or more are not explicit data, the data may be used for measurement of the side waist circumference length, whereby a body size may be measured more exactly.

The controller 130 obtains a length 22 of a long side by using a right-angled triangle, and obtains the left side waist circumference length 20 by multiplying the obtained length 22 of the long side two times.

The right side waist circumference length 40 is obtained equally to the left side waist circumference length 20.

According to the present disclosure, noise occurs in case of the depth camera, whereby a boundary line of a body is not exact. In this case, it is advantageous that the side circumference length may be predicted using a right-angled triangle.

The controller 130 extracts a first length 32 from the body line image and determines the rear waist circumference length 30 by multiplying a specific parameter by the extracted first length 32.

For example, the rear circumference length 30 is obtained using a first length×k parameter. In this case, the k parameter means experimental data based on actually measured data.

The k parameter is changed depending on a body portion. For example, the k parameter of the waist portion is smaller than the k parameter of the bust portion.

The first length 32 means a length when a start point and an end point of the front waist circumference length 10 are connected with each other by a straight line.

The controller 130 determines the front waist circumference length 10, the side waist circumference lengths 20 and 40 and the rear waist circumference length 30 based on the acquired body line image, and measures the waist circumference length among the user's body sizes by combining the front waist circumference length 10, the side waist circumference lengths 20 and 40 and the rear waist circumference length 30.

According to the present disclosure, the bust circumference length and the hip circumference length may be measured in the same manner as the above method.

FIG. 17A and FIG. 17B illustrate that a front waist circumference length, a side waist circumference length, and a rear waist circumference length are measured in accordance with one embodiment of the present disclosure.

FIG. 17A illustrates a method for obtaining a side waist circumference length in detail. Referring to FIG. 17A, the controller 130 the side waist circumference length based on a body line image 1610.

First of all, a description will be given based on that the side waist circumference length is obtained. The side waist circumference length is obtained using a rightangled triangle 1620. The right-angled triangle 1620 includes a first side 1621, a large side 1622 and a first angle 1623.

A key point is to know an actual length of the large side 1622 of the rightangled triangle 1620. First of all, the controller 130 uses data having noise of a predetermined range or more among data acquired from the depth camera for calculation of the side waist circumference length 20. That is, the side waist circumference length is determined based on noise.

For example, if noise is a predetermined range or more, the controller 130 obtains a length of the first side 1621. The length of the first side 1621 may be 10 pixels.

The controller 130 may estimate the first angle 1623 based on experimental data. For example, the first angle may be 15 degrees.

The controller 130 may calculate the actual length of the large side 1622 based on the first side 1621 and the first angle 1623. The actual length of the large side 1622 is obtained by multiplying a length (the number of pixels) of the large side by a pixel length per meter (PPM).

FIG. 17B illustrates a waist circumference length area in detail by cutting the user's waist. Referring to FIG. 17B, the controller 130 obtains the side waist circumference lengths 20 and 40 based on the body line image 1610. The waist circumference length 1630 is equal to front waist circumference length 10+side waist circumference lengths 20 and 40+rear waist circumference length 30.

A method for obtaining the rear waist circumference length 30 will be described in more detail.

The controller 130 extracts a first length 32 from the body line image and determines the rear waist circumference length 30 by multiplying a specific parameter by the extracted first length 32.

For example, the rear circumference length 30 is obtained using a first length×k parameter. In this case, the k parameter means experimental data based on actually measured data. The first length 32 means a length when a start point and an end point of the front waist circumference length 10 are connected with each other by a straight line.

The rear waist circumference length 30 may be considered as a half of an oval circumference length. The oval circumference length is proportional to a length of a long axis. Also, the oval circumference length is proportional to a length of a short axis. A half of the rear waist circumference length 30 may be multiplication of the first length 32 and the k parameter. In this case, the k parameter is determined differently depending on a body portion. For example, the k parameter of the waist portion is smaller than the k parameter of the bust portion. Also, the k parameter is experimental data obtained based on the actually measured data.

FIG. 18 illustrates data of a user's actual height and a measured height according to one embodiment of the present disclosure.

Referring to FIG. 18, if a user is CHC, the user's actual height is 1.78 m. The actual height means a value measured using a tape measure.

A first experimental value becomes 1.78202 m.
A second experimental value becomes 1.77908 m.
A third experimental value becomes 1.76101 m.
A fourth experimental value becomes 1.79096 m.
A fifth experimental value becomes 1.79234 m.

In this way, measurement may be performed up to a tenth experimental value, and an average of errors from the first experimental value to the tenth experimental value becomes 0.015 m.

Even if the user is UEN, ZF, WJU, or PSO, measurement may be performed in the same way.

FIG. 19 illustrates data of a user's actual bust circumference length and a measured bust circumference length according to one embodiment of the present disclosure.

Referring to FIG. 19, if a user is CHC, the user's bust circumference length becomes 0.98 m. The actual bust circumference length means a value measured using a tape measure.

A first experimental value becomes 1.04009 m.
A second experimental value becomes 1.02241 m.
A third experimental value becomes 1.00679 m.
A fourth experimental value becomes 1.01789 m.
A fifth experimental value becomes 1.01635 m.

In this way, measurement may be performed up to a tenth experimental value, and an average of errors from the first experimental value to the tenth experimental value becomes 0.032 m. Even if the user is UEN, ZF, WJU, or PSO, measurement may be performed in the same way.

FIG. 20 illustrates data of a user's actual underbust circumference length and a measured underbust circumference length according to one embodiment of the present disclosure.

Referring to FIG. 20, if a user is CHO, the user's underbust circumference length becomes 0.88 m. The actual underbust circumference length means a value measured using a tape measure.

A first experimental value becomes 0.959572 m.
A second experimental value becomes 0.960445 m.
A third experimental value becomes 0.885358 m.
A fourth experimental value becomes 0.869253 m.
A fifth experimental value becomes 0.903299 m.

In this way, measurement may per formed up to a tenth experimental value, and an average of errors from the first experimental value to the tenth experimental value becomes 0.040 m.

Even if the user is UEN, ZF, WJU, or PSO, measurement may be performed in the same way.

FIG. 21 illustrates data of a user's actual waist circumference length and a measured waist circumference length according to one embodiment of the present disclosure.

Referring to FIG. 21, if a user is CHC, the user's waist circumference length becomes 0.92 m. The actual waist circumference length means a value measured using a tape measure.

A first experimental value becomes 0.985915 m.
A second experimental value becomes 0.939380 m.
A third experimental value becomes 0.929100 m.
A fourth experimental value becomes 0.910563 m.
A fifth experimental value becomes 0.914214 m.

In this way, measurement may be performed up to a tenth experimental value, and an average of errors from the first experimental value to the tenth experimental value becomes 0.025 m.

Even if the user is UEN, ZF, WJU, or PSO, measurement may be performed in the same way.

FIG. 22 illustrates data of a user's actual hip circumference length and a measured hip circumference length according to one embodiment of the present disclosure.

Referring to FIG. 22, if a user is CHC, the user's hip circumference length becomes 0.99 m. The actual hip circumference length means a value measured using a tape measure.

A first experimental value becomes 1.09757 m.
A second experimental value becomes 1.06528 m.
A third experimental value becomes 1.06060 m.
A fourth experimental value becomes 1.04748 m.
A fifth experimental value becomes 1.04226 m.

In this way, measurement may performed up to a tenth experimental value, and an average of errors from the first experimental value to the tenth experimental value becomes 0.039 m.

Even if the user is UEN, ZF, WJU, or PSO, measurement may be performed in the same way.

FIG. 23 illustrates data of an error and exactness of a user's body size measurement data according to one embodiment of the present disclosure.

Referring to FIG. 23, an error rate will be described.
In case of a height, an error rate becomes 0.6%.
In case of a bust circumference length, an error rate becomes 6.1%.
In case of an underbust circumference length, an error rate becomes 4.9%.
In case of a waist circumference length, an error rate becomes 2.3%.
In case of a hip circumference length, an error rate becomes 2.0%.

Exactness will be described. Exactness means a value obtained by subtracting an error rate from 100%.
In case of a height, exactness becomes 99.4%.
In case of a bust circumference length, exactness becomes 93.9%.
In case of an underbust circumference length, exactness becomes 95.1%.
In case of a waist circumference length, exactness becomes 97.7%.
In case of a hip circumference length, exactness becomes 98.0%.

FIG. 24 illustrates data of an error and exactness of a user's body size measurement data according to one embodiment of the present disclosure.

Referring to FIG. 24, if a user is UEK, the user's actual height becomes 1.53 m. The actual key means a value measured using a tape measure.

A first experimental value becomes 1.52192 m.
A second experimental value becomes 1.53040 m.
A third experimental value becomes 1.54128 m.
A fourth experimental value becomes 1.53899 m.
A fifth experimental value becomes 1.54272 m.

An average of errors from the first experimental value to the fifth experimental value becomes 0.00933063 m.

Even if the user is KBR, ZU, or CHO, measurement may be performed in the same way.

Next, an error rate will be described.
In case of a height, an error rate becomes 0.2%.
In case of a shoulder length, an error rate becomes 1.6%.
In case of an arm length, an error rate becomes 2.5%.

Exactness will be described. Exactness means a value obtained by subtracting an error rate from 100%.
In case of a height, exactness becomes 99.8%.
In case of a shoulder length, exactness becomes 98.4%.
In case of an arm length, exactness becomes 97.5%.

Figure 25:
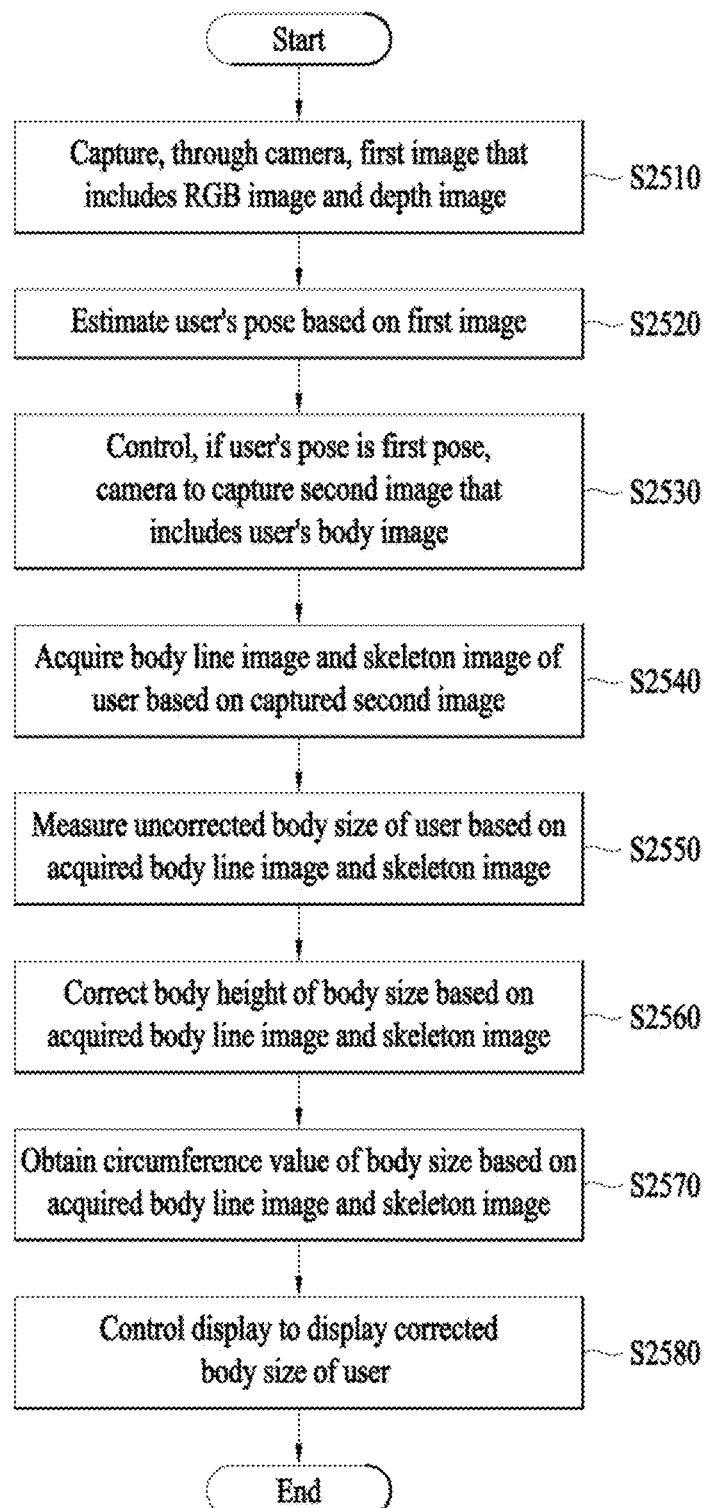
FIG. 25 is a flow chart illustrating a method for controlling a body measurement device according to one embodiment of the present disclosure.

FIG. 25 is a flow chart illustrating a method for controlling a body measurement device according to one embodiment of the present disclosure.

*Since the body measurement device is based on an RGB image and a depth image, it is difficult to measure an accurate body size when the user is dressed, particularly in loose clothes that do not fit the body (hereinafter, referred to as "loose fit state").

In addition to the clothes, when the user has a hair volume formed at a significant height and wears shoes, it is difficult to obtain the actual height of the user in consideration of such noise.

Therefore, there is a desire for a process of correcting an uncorrected body size that is a body size simply acquired from an RGB image and a depth image to obtain a corrected body size, that is, an actual body size.

As described above, a process of correcting an acquired body height to an actual body height, a process of correcting an acquired body circumference to an actual body circumference, or a process of estimating the actual body height or the body circumference directly from other factors may be required.

Like operations S210 through S240 of FIG. 2, a body line image of a user is acquired in operations S2510 through S2540. As described above, when a user's pose estimated based on a first image is a first pose, a second image may be captured, so that a body size is estimated based on the captured second image.

The body line image acquired through operations S2510 through S2540 may correspond to an uncorrected body size including noise due to the loose clothes, shoe height, and hair volume. Thus, a process of removing the noise or a process of obtaining a body size without correction based on a noise-free body size may be required.

To correct the body size, an RGB image and a depth image, for example, a body line image and a skeleton image obtained from the images may be used. The body line image and the skeleton image are defined as a source image. Based on the source image, body sizes including an actual body height and an actual circumference of the user may be obtained. An actual body size may be obtained by using either one or both body line image and skeleton image.

When the first image is acquired using the camera and the first image corresponds to a key pose as illustrated in FIG. 2, a second image may be acquired to measure a body size. Also, when the first image corresponds to the key pose, the body size may be measured from the acquired first image as necessary.

Figure 26:
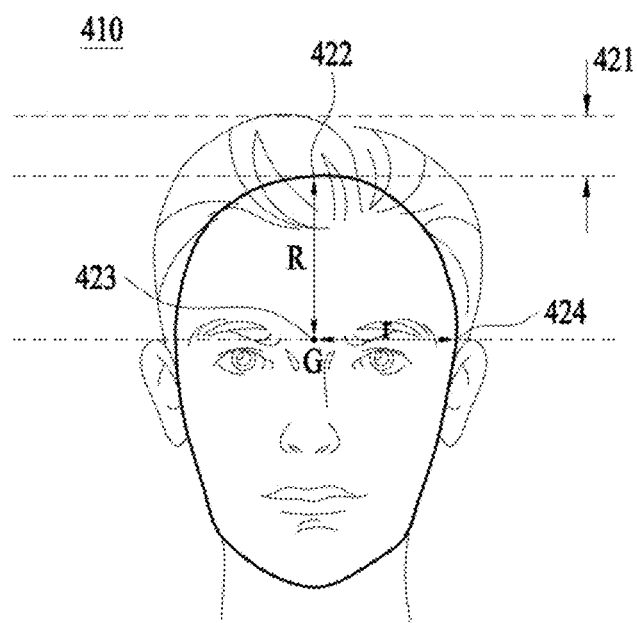
FIG. 26 illustrates face information for obtaining a hair volume value according to one embodiment of the present disclosure.

FIG. 26 illustrates face information 410 for obtaining a hair volume value 421 according to one embodiment of the present disclosure.

The controller 130 may obtain the hair volume value 421 of the user from a source image and correct an uncorrected body height to a corrected body height using the obtained hair volume value 421.

Once the hair volume value 421 is obtained, a top 422 of a user's head may be acknowledged. For example, the corrected body height may be a height to the top 422 obtained by subtracting the hair volume value 421 from the uncorrected body height.

The hair volume value 421 may be obtained based on the face information 410 of the source image. In other words, the height of the top 422 may be stochastically determined based on the face information 410.

The face information 410 for obtaining the hair volume value 421 may be acquired based on a distance from a nose 423 to an ear 424. When a horizontal line passing through the ear 424 meets the nose 423 on a point G, a distance R from the point G to the top 422 may be statistically a value obtained by multiplying a distance r from the point G to the ear 424 by a predetermined constant. The predetermined constant may be, for example, 1.35.

Coordinates of the nose 423 and the ear 424 may be obtained by the controller 130 based on an RGB image, a depth image, or a skeleton image. The obtained coordinates of the nose 423 and the ear 424 may be based on a case in which the face information 410 is front face information of the source image.

Figure 27A:
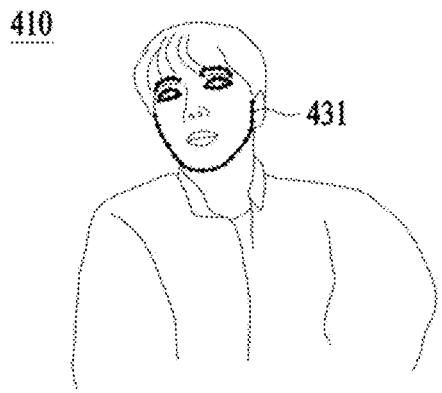
FIG. 27A and FIG. 27B illustrate a method for obtaining a hair volume value according to one embodiment of the present disclosure.
Figure 27B:
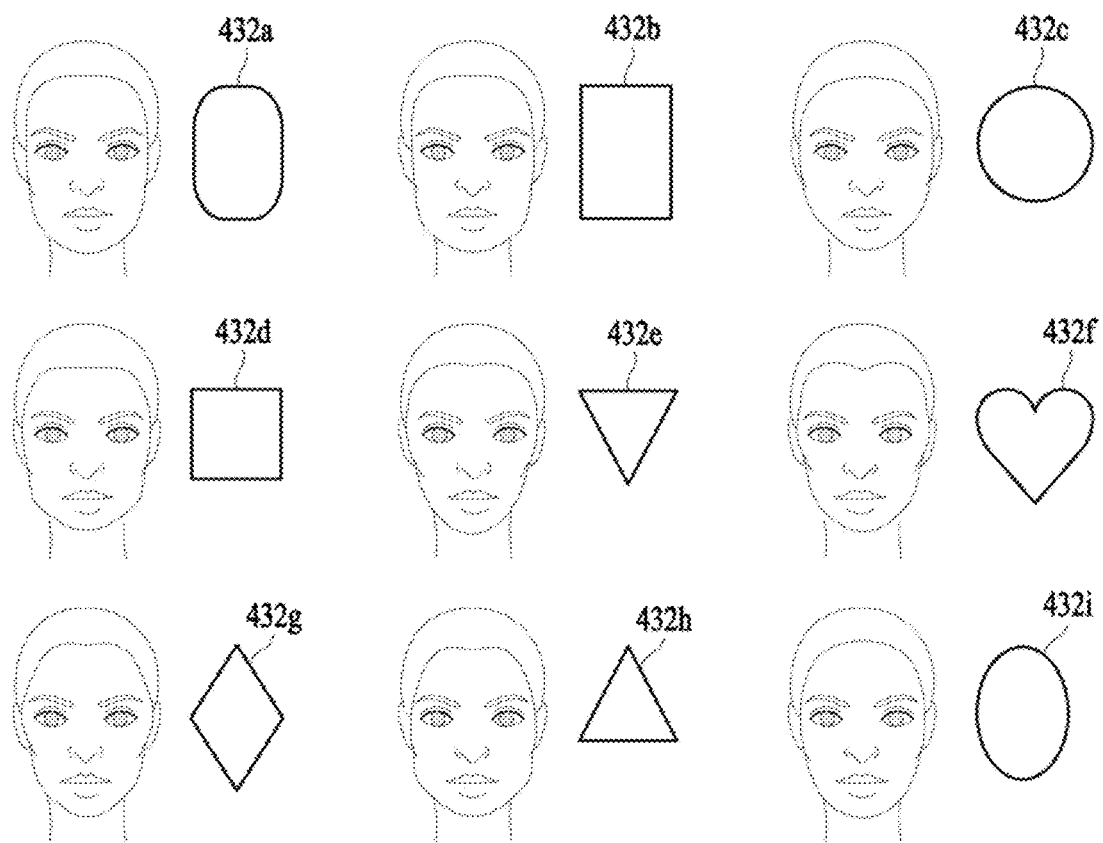

FIG. 27A and FIG. 27B illustrate a method for obtaining a hair volume value 421 according to one embodiment of the present disclosure.

As another method for obtaining the hair volume value 421, a face shape 432 may be used for determining a hair volume. Statistically, when the face shape 432 is specified, a shape and a length to a top 422 of a head may be fixed. In this instance, the face shape 432 may be determined based on a jawline shape 431.

When the jawline shape 431 of a user is included in acquired face information 410, the controller 130 may determine a jawline shape corresponding to the jawline shape 431 among a plurality of prestored jawline shapes as shown in FIG. 27B, and obtain the hair volume value 421 by applying a height of the top 422 of a face shape having the corresponding jawline shape.

Although FIG. 27B shows nine face shapes 432a through 431i as an example, fewer or more samples may be stored in some cases.

Also, the height of the top 422 corresponding to the jawline shape 431 may reflect a face size. Even when the jawline shape 431 or the face shape corresponds to prestored information, if the face size differs, the height of the top 422 may be changed. In this case, a face size factor may be applied to obtain a height value of the top 422. For example, when a ratio between a face size acquired from a source image and a prestored corresponding face size is 0.8:1.0, an actual height value of the top 422 may be obtained by multiplying the prestored height of the top 422 by 0.8.

A ratio of the face size may be calculated using a ratio of a value of the distance from the nose 423 to the ear 424 described with reference to FIG. 26.

Figure 28A:
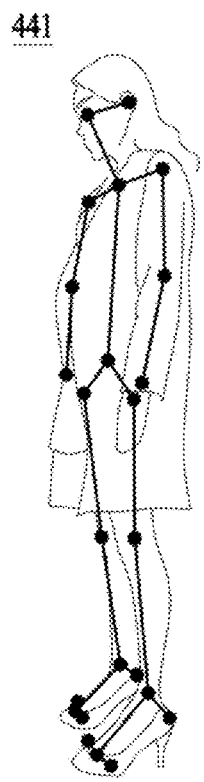
FIG. 28A and FIG. 28B illustrate a skeleton image for correcting a body height and a partial enlarged view according to one embodiment of the present disclosure.
Figure 28B:
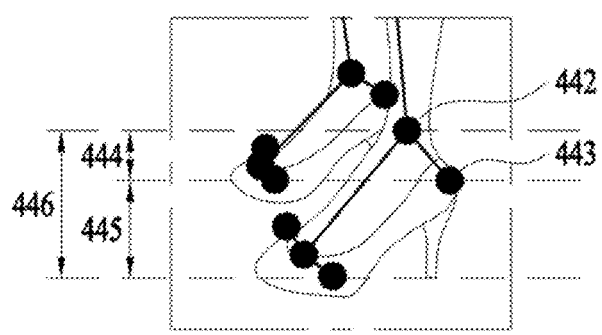

FIG. 28A and FIG. 28B illustrates a skeleton image 441 for correcting a body height and a partial enlarged view according to one embodiment of the present disclosure.

As described above, a body height may be corrected in consideration of a shoe height.

A shoe height value 445 may be obtained based on a skeleton image 441. The controller 130 may obtain the shoe height value 445 based on a difference between a distance from a lateral malleolus point 442 of the skeleton image 441 to a floor and a distance 444 from the lateral malleolus point 442 to a sole 443.

In the above-described methods, an uncorrected body height value may be corrected by applying the acquired hair volume value 421 and shoe height value 445 thereto. Through this, an actual body height of the user may be estimated.

FIG. 29A and FIG. 29B illustrates experimental values of body height estimation according to one embodiment of the present disclosure. FIG. 29A shows factors used in body height estimation associated with a hair volume and errors in estimated values. FIG. 29B illustrates factors used in the body height estimation.

In addition to the method for correcting the body height using the hair volume value 421 and the shoe height value, the body height may also be estimated using specific factors of an uncorrected body size.

For example, the controller 130 may acquire a corrected body height by applying an actual measured value acquired from a source image to a predetermined function.

The actual measured value may be applied to the following equation.

$$y_i = X_i^T \beta + \varepsilon_i$$

In this equation, $y_i$ denotes an actual height, $X_i^T$ denotes an actual measured value, $\beta$ denotes a proportion, and $\varepsilon_i$ denotes noise.

For example, the controller 130 may obtain the actual height value by applying a value of a length from a center of a hand to a shoulder of a skeleton image as the actual measured value. The actual measured value may be a chest value, a neck-shoulder-elbow-wrist value, a back-shoulder-neck crossing value, a neck-to-gluteal-hip value, a natural waist value, a maximum hip value, a natural waist rise value, an upper arm value, and a wrist value of the user obtained from the source image. The controller 130 may apply at least one of the aforementioned values to the above equation, thereby estimating the actual height.

Empirically, it can be confirmed that the error is minimum when the value of the length from the center of the hand to the shoulder is included.

Referring back to FIG. 25, the body height may be acquired using the above-described method. Also, values related to the length, that is, length values of the body size may be obtained as the same value substantially irrespective of whether the user is dressed. The length values may be obtained from the source image, for example, an RGB image, a depth image, a body line image, and a skeleton image. The length values may include, for example, a shoulder length, an arm length, and a leg length.

In a case in which the user is dressed, values related to a circumference, that is, circumference values of the body size obtained from the source image may have relatively large errors. Thus, the circumference value may be estimated from the length value which is relatively accurate value.

The circumference value may include, for example, a bust circumference, a waist circumference, and a hip circumference of the body size.

A probability scheme or a deep-learning scheme may be used to obtain the circumference value based on the length value. For example, a circumference value corresponding to an applied length value at a highest probability of cumulative information may be obtained. In this example, the cumulative information may be stored in advance. When the deep-learning scheme is used, a result circumference value may be obtained based on the length value being applied and thus, specified as the body size.

Figure 30:
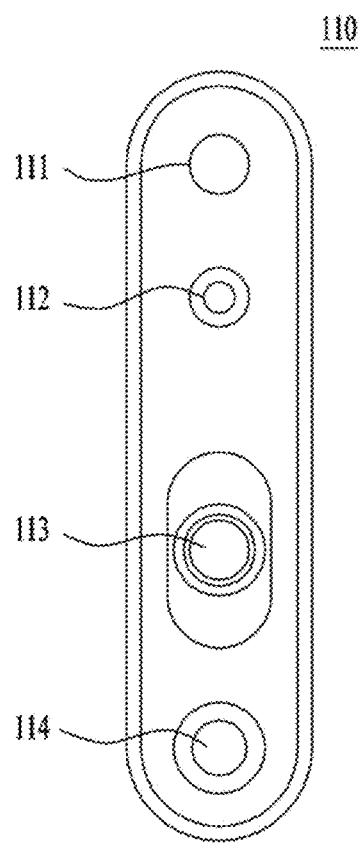
FIG. 30 illustrates a structure of a camera of a body measurement device according to one embodiment of the present disclosure.

FIG. 30 illustrates a structure of a camera of a body measurement device according to one embodiment of the present disclosure.

Referring to FIG. 30, the camera 110 includes an RGB camera 111, a first IR camera 112, an IR light 113, and a second IR camera 114.

In this case, the camera 110 is vertically provided in the body measurement device 100. The camera 110 should be provided vertically to acquire a depth image with more stereoscopic effect when capturing a person image.

If the camera 110 is used, map type 3D depth information may be output, and noise based on a light change is less acquired than a stereo vision technology and is not the result based on image processing so that it is advantageous that textureless or occlusion is not acquired.

Figure 31A:
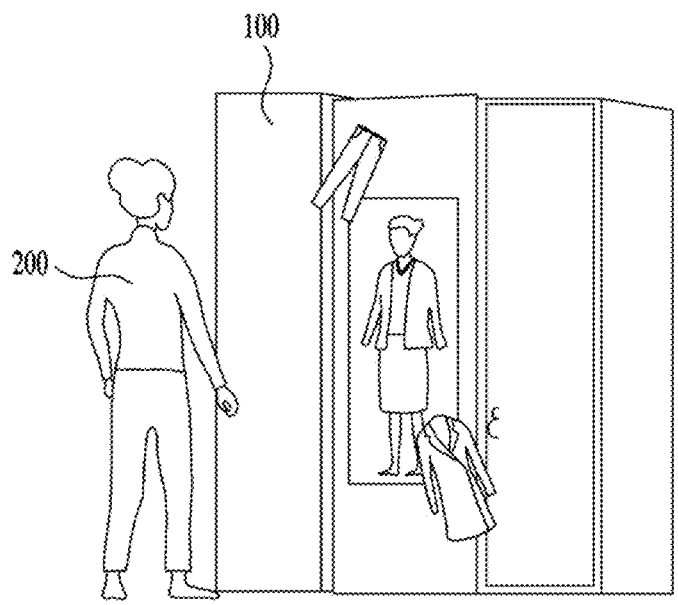
FIG. 31A and FIG. 31B illustrate a use example of a body measurement device according to one embodiment of the present disclosure.
Figure 31B:
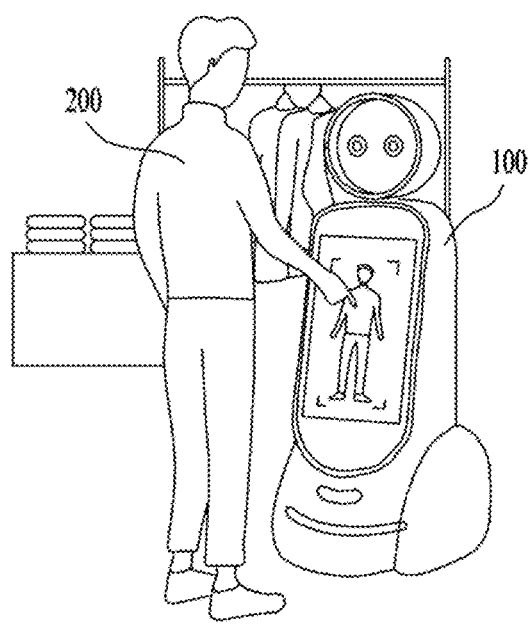

FIG. 31A and FIG. 31B illustrates a use example of a body measurement device according to one embodiment of the present disclosure.

FIG. 31A illustrates that the body measurement device 100 is provided in a stylus, and a user 200 stands in front of the body measurement device 100. As shown in FIG. 31A, the camera 110 of the body measurement device 100 measures a body size by capturing the user's whole body image.

FIG. 31B illustrates that the body measurement device 100 is provided in a tailor bot in a clothes store and the user 200 stands in front of the body measurement device 100. Referring to FIG. 31B, the camera 110 of the body measurement device 100 measures a body size of the user by capturing the user's upper body or whole body image.

The tailor bot is a guide robot for recommending clothes for the user 200 and executing virtual fitting, and may measure a body size and perform virtual fitting by using an avatar corresponding to a user on the screen.

Figure 32A:
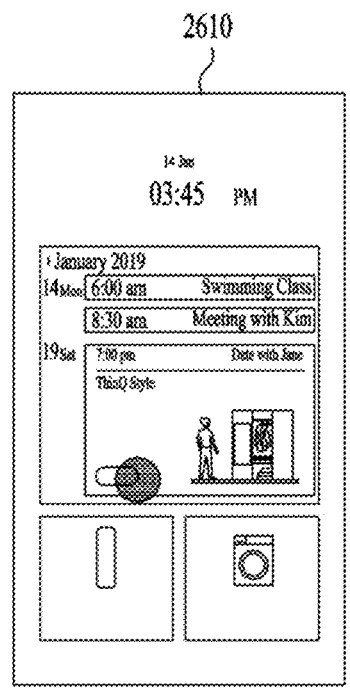
FIG. 32A and FIG. 32B illustrate an execution screen of a body measurement device according to one embodiment of the present disclosure.
Figure 32B:
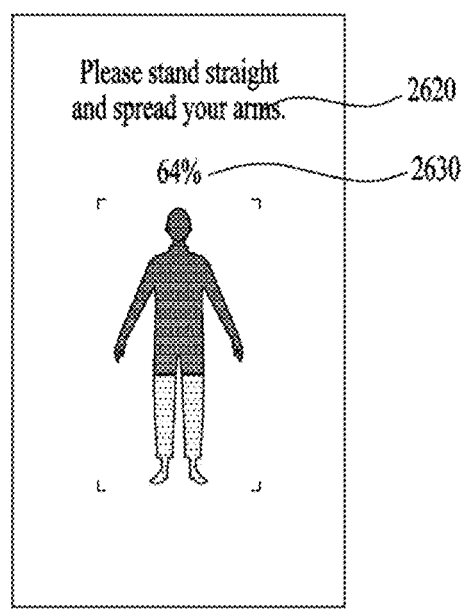

FIG. 32A and FIG. 32B illustrates an execution screen of a body measurement device according to one embodiment of the present disclosure.

FIG. 32A illustrates an execution screen of the body measurement device. Referring to FIG. 32A, if the body measurement device 100 is executed, the controller 130 displays the current time, Jan. 14, 2019, 03:45, PM, and an important meeting schedule.

FIG. 32B illustrates that a procedure of executing a body measurement process is displayed when a user stands in front of the body measurement device 100.

If the user stands in front of the body measurement device 100, the controller 130 displays a text 2620 that includes a content indicating that a user stands straight and spreads his/her arms. Also, the controller 130 displays an image 2430 indicating the procedure of executing the body measurement process, for example, 64%. In this case, 0% means that the body measurement process starts, and 100% means that the body measurement process is completed.

Figure 33:
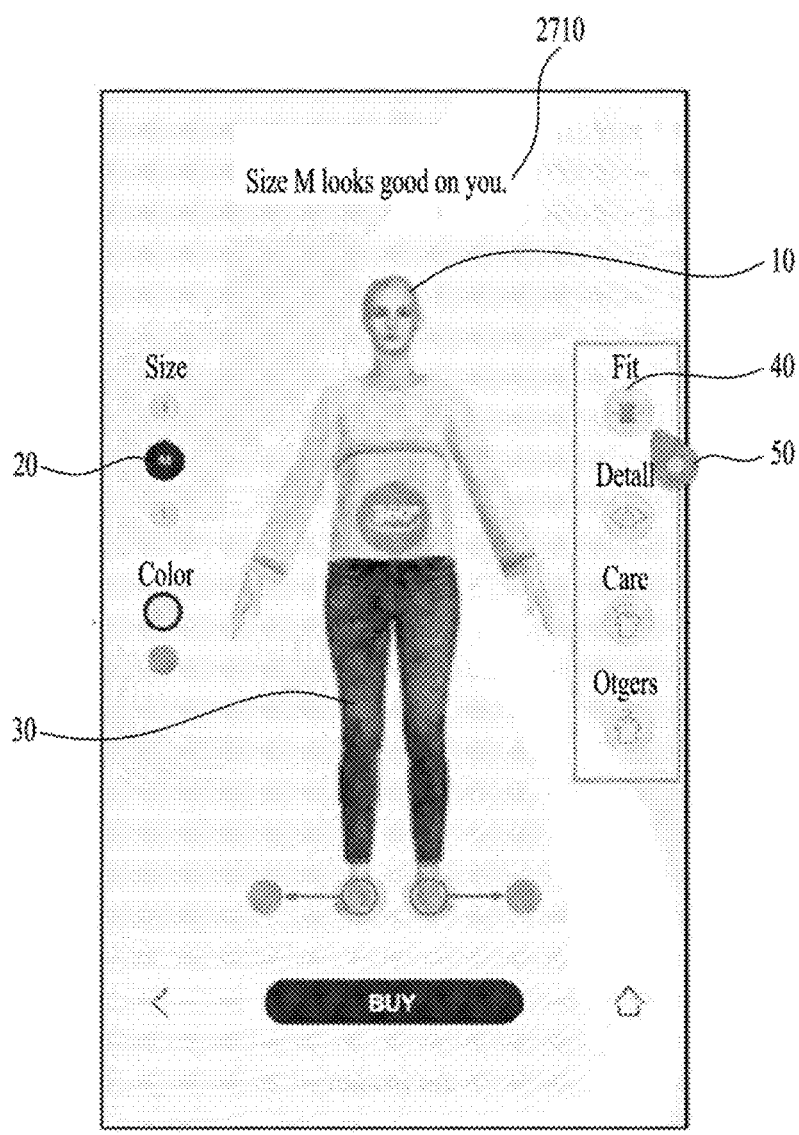
FIG. 33 illustrates an execution screen of a body measurement device according to one embodiment of the present disclosure.

FIG. 33 illustrates an execution screen of a body measurement device according to one embodiment of the present disclosure.

Referring to FIG. 33, the controller 130 displays an avatar 10 having the same body size as the user's body size on the screen.

For example, the user's body size includes a height of 172 cm, a bust circumference length of 101 cm, a waist circumference length of 94 cm, and a hip circumference length of 102 cm. In this case, clothes may be pants.

The controller 130 determines the most suitable clothes size based on the user's body size, and displays a text 2710 recommending clothes of M size for the user.

The size may be L, M and S, and if the user selects a specific size icon 20, the controller 130 displays an avatar 10 who wears clothes corresponding to the size icon 20 selected by the user. In this case, the clothes may be pants.

If an input 50 for selecting a fitting icon 40 is received from the user, the controller 130 displays an image indicating that the user wears pants. This will be described later with reference to FIG. 34.

Figure 34:
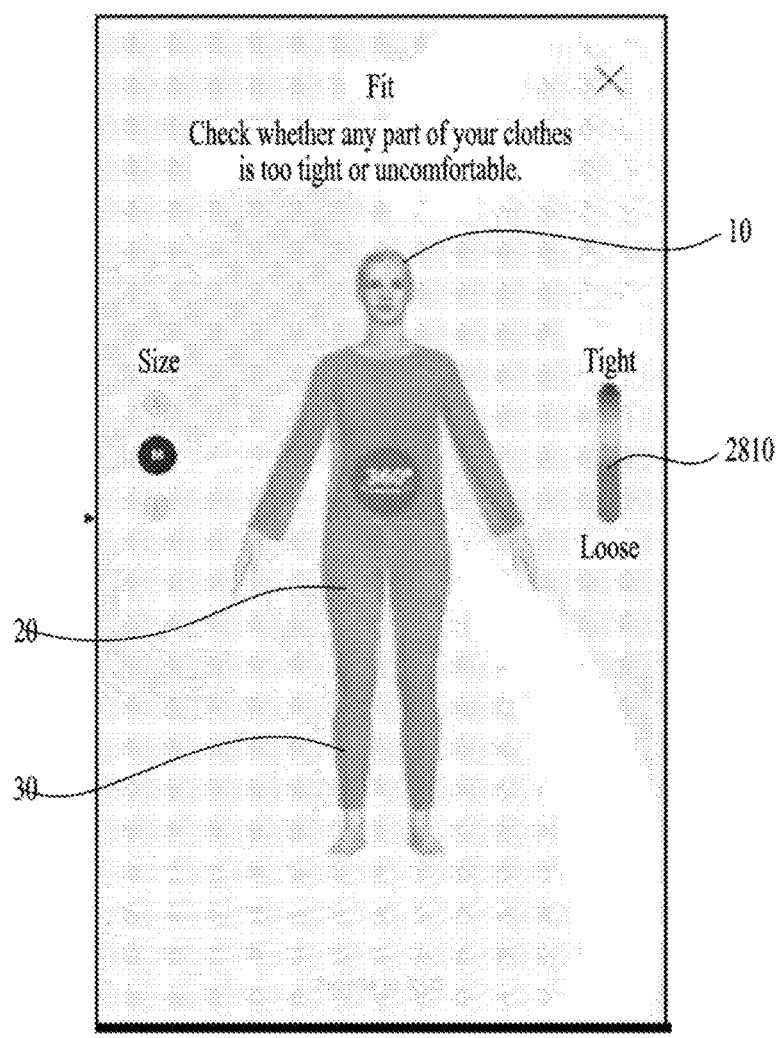
FIG. 34 illustrates an execution screen of a body measurement device according to one embodiment of the present disclosure.

FIG. 34 illustrates an execution screen of a body measurement device according to one embodiment of the present disclosure.

FIG. 34 illustrates a wearing state when a user wears pants of a specific size. The controller 130 displays a progressive bar 2810 indicating a wearing state. For example, the specific size may be M.

The progressive bar 2810 may be changed from a first color to a second color, wherein the first color means that clothes worn by the user are tight for the user, and the second color means that clothes worn by the user are loose for the user. A color change from the first color to the second color may be changed to a gradation effect.

When a user avatar 10 wears pants, the controller 130 displays a graphic image 20 indicating a wearing state per body portion on the avatar image 10. The graphic image 20 may be displayed differently depending on the wearing state per body portion.

For example, when the user avatar 10 wears pants, the controller 130 may display the graphic image 20, which includes a color meaning loose, on an upper portion of the pants, and may display a graphic image 30, which includes a color meaning tight, on a lower portion of the pants.

According to the present disclosure, when the user avatar 10 wears clothes of a specific size, the controller 130 displays a graphic image indicating a wearing state per body portion. Therefore, since the user may intuitively know whether clothes are tight or loose even though the user does not wear the clothes, user convenience may be improved.

According to one embodiment of the present disclosure, if the user takes a specific pose, the user's image is captured. After the RGB image and the depth image are combined with each other, the user's body line image may be acquired from the captured image, and the user's body size may be measured based on the acquired body line image. Therefore, the user's image may be captured by a simple operation and an exact body size may be measured, whereby user convenience may be improved.

According to another embodiment of the present disclosure, a skeleton image is extracted from the captured image, and the skeleton image, the RGB image and the depth image may be combined with one another to acquire the user's body line image. Therefore, the user's body size may be measured more exactly, whereby user convenience may be improved.

According to still another embodiment of the present disclosure, a first length may be extracted from a body line image, and a specific parameter may be multiplied by the first length to determine a rear waist circumference length. Therefore, a waist circumference length which is invisible from a front image may exactly be measured, whereby user convenience may be improved.

The body measurement device and the method for controlling the same according to the present disclosure are not limited to the aforementioned embodiments, and all or some of the aforementioned embodiments may selectively be configured in combination so that various modifications may be made in the aforementioned embodiments.

Meanwhile, the method according to the present specification may be implemented as code that can be written on a processor-readable recording medium and thus read by a processor provided in a network device. The processor-readable recording medium may be any type of recording device in which data are stored in a processor-readable manner. The processor-readable recording medium may include, for example, read only memory (ROM), random access memory (RAM), compact disc read only memory (CD-ROM), magnetic tape, a floppy disk, and an optical data storage device, and may be implemented in the form of a carrier wave transmitted over the Internet. In addition, the processor-readable recording medium may be distributed over a plurality of computer systems connected to a network such that processor-readable code is written thereto and executed therefrom in a decentralized manner.

In addition, it will be apparent that, although the preferred embodiments have been shown and described above, the present specification is not limited to the above-described specific embodiments, and various modifications and variations can be made by those skilled in the art to which the present disclosure pertains without departing from the gist of the appended claims. Thus, it is intended that the modifications and variations should not be understood independently of the technical spirit or prospect of the present specification.

Various embodiments have been described in the best mode for carrying out the invention.

The present disclosure is used in a series of body measurement device-related fields in which an RGB image and a depth image are combined with each other to acquire a user's body line image, and a body size of the user is measured based on the acquired body line image.

Those skilled in the art will appreciate that the present disclosure may be carried out in other specific ways than those set forth herein without departing from the spirit and essential characteristics of the present disclosure. Therefore, the scope of the invention should be determined by the appended claims and their legal equivalents, rather than by the above description, and all changes that fall within the meaning and equivalency range of the appended claims are intended to be embraced therein.

What is claimed is:

1. A body measurement device comprising:
   a camera configured to capture an image that includes an RGB image and a depth image;
   a display; and
   a controller configured to:
   acquire a source image that includes a skeleton image and a body line image of a user based on the captured image, wherein the source image includes coordinate information of a nose and an ear of the user and a jawline shape of the user,
   acquire a body size including a body height based on the source image, wherein the body height includes an uncorrected body height and a corrected body height, and
   cause the display to display the body size, wherein the controller is further configured to obtain a hair volume value of the user based on face information from the source image and correct the uncorrected body height to the corrected body height based on the hair volume value, wherein the hair volume value is obtained based on the jawline shape of the user or a distance from the nose of the user to the ear of the user.

2. The body measurement device of claim 1, wherein the hair volume value is obtained by multiplying the distance from the nose to the ear by a predetermined constant.

3. The body measurement device of claim 1, wherein the controller is further configured to determine the jawline shape of the user among nine jawline shapes stored in advance, and to obtain the hair volume value based on information on the determined jawline shape.

4. The body measurement device of claim 1, wherein the controller is further configured to obtain a shoe height value of the user from the source image and correct the uncorrected body height to the corrected body value based on the shoe height value.

5. The body measurement device of claim 4, wherein the controller is further configured to obtain a shoe height value of the user from the skeleton image of the source image.

6. The body measurement device of claim 5, wherein the controller is further configured to obtain the shoe height value based on a difference between a distance from a lateral malleolus point of the skeleton image to a floor and a distance from the lateral malleolus point to a sole.

7. The body measurement device of claim 1, wherein the controller is further configured to estimate a pose of the user based on the captured image and to control the camera to additionally capture an image when the estimated pose of the user is included in a preset pose.

8. The body measurement device of claim 7, wherein the controller is further configured to control the camera to capture a plurality of additional images, and the source image is acquired based on the plurality of additional images.

9. A body measurement device comprising:
   a camera configured to capture an image that includes an RGB image and a depth image;
   a display; and
   a controller configured to acquire a source image that includes a skeleton image and a body line image of a user based on the captured image, acquire a body size including a body height based on the source image, and control the display to display the body size,
   wherein the body height includes an uncorrected body height and a corrected body height, and
   wherein the controller is configured to obtain a value of a length from a center of a hand to a shoulder of the user from the source image and to correct the uncorrected body height to the corrected body height based on the obtained value of the length from the center of the hand to the shoulder.

10. The body measurement device of claim 9, wherein the controller is further configured to obtain a chest value, a neck-shoulder-elbow-wrist value, a back-shoulder-neck crossing value, a neck-to-gluteal-hip value, a natural waist value, a maximum hip value, a natural waist rise value, an upper arm value, and a wrist value of the user from the source image, and correct the uncorrected body height to the corrected body height based on the obtained value and the value of the length from the center of the hand to the shoulder.

* * * * *